US012390139B2

(12) United States Patent
Itagaki et al.

(10) Patent No.: US 12,390,139 B2
(45) Date of Patent: Aug. 19, 2025

(54) BIOLOGICAL SIGNAL MONITORING WEAR

(71) Applicant: Toray Industries, Inc., Tokyo (JP)

(72) Inventors: Ichiro Itagaki, Tokyo (JP); Shinichi Otake, Tokyo (JP); Hideo Nakata, Tokyo (JP)

(73) Assignee: Toray Industries, Inc., Tokyo (JP)

( * ) Notice: Subject to any disclaimer, the term of this patent is extended or adjusted under 35 U.S.C. 154(b) by 434 days.

(21) Appl. No.: 17/908,009

(22) PCT Filed: Feb. 26, 2021

(86) PCT No.: PCT/JP2021/007372
§ 371 (c)(1),
(2) Date: Aug. 30, 2022

(87) PCT Pub. No.: WO2021/177171
PCT Pub. Date: Sep. 10, 2021

(65) Prior Publication Data
US 2023/0086291 A1  Mar. 23, 2023

(30) Foreign Application Priority Data
Mar. 2, 2020 (JP) ................................ 2020-035341

(51) Int. Cl.
*A61B 5/256* (2021.01)
*A61B 5/00* (2006.01)
(Continued)

(52) U.S. Cl.
CPC ................ *A61B 5/256* (2021.01); *A61B 5/27* (2021.01); *A61B 5/273* (2021.01); *A61B 5/282* (2021.01);
(Continued)

(58) Field of Classification Search
CPC ........... A61B 5/256; A61B 5/27; A61B 5/273; A61B 5/282; A61B 5/6804; A61B 5/24; A61B 5/318; A61B 5/333
See application file for complete search history.

(56) References Cited

U.S. PATENT DOCUMENTS

2014/0012145 A1  1/2014  Kurzweil et al.
2016/0007919 A1  1/2016  Pernu et al.
(Continued)

FOREIGN PATENT DOCUMENTS

GB  2499406 A  8/2013
JP  H06-070897 A  3/1994
(Continued)

OTHER PUBLICATIONS

Extended European Search Report dated Feb. 15, 2024, of counterpart European Patent Application No. 21763897.2.
(Continued)

*Primary Examiner* — Paula J Stice
(74) *Attorney, Agent, or Firm* — DLA Piper LLP (US)

(57) ABSTRACT

A biological signal monitoring wear includes: a plurality of electrodes; an electrically connecting unit configured to electrically connect a biological signal measurement instrument to the electrodes; and a wear main body to which the electrically connecting unit is detachably attached. The electrically connecting unit includes: a sheet electrical insulator having flexibility; a plurality of electrode connectors formed on a first surface of both surfaces of the electrical insulator, the electrode connectors configured to connect the respective electrodes; an instrument connector formed on a second surface of both surfaces of the electrical insulator, the instrument connector configured to detachably connect the biological signal measurement instrument; and an electrical conductor formed in the electrical insulator, the electrical
(Continued)

conductor configured to electrically connect the electrode connectors to the instrument connector.

13 Claims, 14 Drawing Sheets

(51) Int. Cl.
    *A61B 5/27*     (2021.01)
    *A61B 5/273*     (2021.01)
    *A61B 5/282*     (2021.01)

(52) U.S. Cl.
    CPC ...... *A61B 5/6804* (2013.01); *A61B 2562/225* (2013.01)

(56) References Cited

U.S. PATENT DOCUMENTS

| | | |
|---|---|---|
| 2016/0374615 A1 | 12/2016 | Tsukada et al. |
| 2017/0143977 A1 | 5/2017 | Kaib et al. |
| 2017/0340226 A1 | 11/2017 | Takagahara et al. |
| 2018/0249767 A1 | 9/2018 | Begriche et al. |
| 2018/0296160 A1 | 10/2018 | Tsukada et al. |
| 2019/0261921 A1 | 8/2019 | Otsuka et al. |
| 2019/0298987 A1 | 10/2019 | Freeman et al. |
| 2020/0187803 A1 | 6/2020 | Komatsu et al. |

FOREIGN PATENT DOCUMENTS

| | | |
|---|---|---|
| JP | 2013-185283 A | 9/2013 |
| JP | 2016-179250 A | 10/2016 |
| JP | 2017089052 A | 5/2017 |
| JP | 2017-148576 A | 8/2017 |
| JP | 6342596 B1 | 6/2018 |
| JP | 2018114302 A | 7/2018 |
| JP | 2018-153666 A | 10/2018 |
| JP | 2019014978 A | 1/2019 |
| JP | 2019-131914 A | 8/2019 |
| WO | 2017/007016 A1 | 1/2017 |
| WO | 2018/047814 A1 | 3/2018 |
| WO | 2019/035420 A1 | 7/2020 |

OTHER PUBLICATIONS

International Search Report dated May 18, 2021 in counterpart International Application No. PCT/JP2021/007372.
Written Opinion dated May 18, 2021 in counterpart International Application No. PCT/JP2021/007372.
Office Action dated May 2, 2025, from counterpart Japanese Patent Application No. 2025-016066.
Chinese Office Action dated Jun. 6, 2025, from counterpart Chinese Patent Application No. 2021800181081.

FIG.16

ECG Analysis Report

TEST INFORMATION

| | | | |
|---|---|---|---|
| NAME | : | START TIME | : 2019/05/31 12:21 |
| ID | : | END TIME | : 2019/06/03 11:02 |
| AGE | : | MEASUREMENT PERIOD | : 70 HOURS 41 MINUTES 15 SECONDS (NOISE RATE: 0%) |
| SEX | : MALE | ACQUISITION DATE | : 2019/06/03 10:43:21 |
| NAME OF INSTITUTION | : | PERSON IN CHARGE | : |
| ELECTROCARDIOGRAM ACQUISITION RATE | : 99.82% | | |

CARDIAC BEAT INFORMATION

| | | | |
|---|---|---|---|
| MAXIMUM | : 138 BEATS/MIN. (06/02 00:34) | TOTAL BEAT NUMBER | : 305867 BEATS |
| AVERAGE | : 75.0 BEATS/MIN. | R-R EXTENSION | : 8 TIMES |
| MINIMUM | : 4 BEATS/MIN. (06/02 05:26) | MAXIMUM | : 192.4 SECONDS (06/02 05:26) |

PVC FINAL RESULT

| | | | |
|---|---|---|---|
| SINGLE CONTRACTION | : 441 TIMES | RonT | : 0 TIMES |
| BIGEMINAL PULSE | : 15 TIMES | LONGEST CONTRACTION | : 3 CONTRACTIONS (06/01 06:16) |
| DOUBLE CONTRACTION | : 38 TIMES | INCIDENCE RATE | : 0.2% |
| TRIPLE OR MORE CONTRACTION | : 3 TIMES | TOTAL NUMBER | : 541 CONTRACTIONS |

PAC FINAL RESULT

| | | | |
|---|---|---|---|
| SINGLE CONTRACTION | : 230 TIMES | LONGEST CONTRACTION | : 5 CONTRACTIONS (06/01 17:44) |
| DOUBLE CONTRACTION | : 90 TIMES | INCIDENCE RATE | : 0.1% |
| TRIPLE OR MORE CONTRACTION | : 9 TIMES | TOTAL NUMBER | : 441 CONTRACTIONS |

ST LEVEL

| | | | |
|---|---|---|---|
| Ch 1 MINIMUM | : −3.92 mV (06/02 00:39) | Ch 1 MAXIMUM | : 4.36 mV (06/02 14:57) |
| Ch 2 MINIMUM | : − | Ch 2 MAXIMUM | : − |

ATRIAL FIBRILLATION SUMMARY

| | | | |
|---|---|---|---|
| MAXIMUM CARDIAC BEAT NUMBER | : 0 BEAT/MIN. | MAXIMUM RETENTION TIME | : 00:00:00 |
| AVERAGE CARDIAC BEAT NUMBER | : 0 BEAT/MIN. | INCIDENCE RATE | : 0.00% |

ANALYSIS CONDITION

| | | | | |
|---|---|---|---|---|
| RECORDING CH : 1CH | R-R EXTENSION : 20 SECONDS OR LONGER | PVC DETECTION : QRS INTERVAL OF 100 ms OR MORE | REFRACTORY PERIOD : 300ms | |
| PAC DETECTION : 70% OF R-R AVERAGE IN 120 CARDIAC BEATS BEFORE AND AFTER TARGETED WAVEFORM | | R WAVE DETECTION SENSITIVITY : LOW | ANALYSIS : 1 Ch | |

☐ WITHIN NORMAL RANGE ☐ OBSERVATION NECESSARY ☐ REGULAR OBSERVATION NECESSARY ☐ CLOSE EXAMINATION NECESSARY ☐ MEDICAL TREATMENT NECESSARY ☐ REEXAMINATION NECESSARY

COMMENTS

DOCTOR'S NAME          DATE   YEAR   MONTH   DAY

BIOLOGICAL SIGNAL MONITORING WEAR

TECHNICAL FIELD

This disclosure relates to a biological signal monitoring garment used to monitor a biological signal such as an electrocardiogram.

BACKGROUND

As for the method to measure biological signals such as a cardiac beat and an electrocardiogram comfortably and conveniently under an environment of a normal daily life, the use of a so-called wearable biological signal monitoring system having an electrode and a measurement instrument attached to a cloth or a belt has been attempted.

In general, the garment used in the wearable biological signal monitoring system (i.e., biological signal monitoring garment) is divided into an electrode portion that contacts with a living body, a terminal connector to which a terminal for measuring a biological signal is attached, a lead wire that connects the electrode portion with the terminal connector, and a body fabric portion that serves as a base to which the electrode portion, the terminal connector, and the lead wire are attached. In these components of the biological signal monitoring garment, only the electrode portion, the terminal connector, and the lead wire are provided with an electric conductivity, while the body fabric portion is formed of an electrically insulating material. By configuring the biological signal monitoring garment in this way, an intended biological signal can be obtained only from the electrode portion.

To monitor the biological signal for a long period of time such as 1 week or longer using the biological signal monitoring garment, it is important that this system can be taken off upon taking a bath or the like, and a sensor such as the electrode can be readily positioned even by a subject not having a specialized knowledge, and a stable information with less noise can be obtained so that the disease can be diagnosed by a method like an electrocardiogram analysis. To fulfil these requirements, many developments have been made with regard to the biological signal monitoring garment incorporated with a sensor such as the electrode. Hereinafter, some representative conventional techniques relating to the biological signal monitoring garment will be described.

Japanese Patent Application Laid-open No. H06-70897 discloses an electrocardiogram measurement garment equipped with a tightening means for bringing a sheet portion having an electrode portion into close contact with a subject's body surface. In that electrocardiogram measurement garment, the electrode portion and a lead wire can be freely attached to and detached from the electrocardiogram measurement garment by inserting the electrode portion having a button shape and the fixed lead wire through a slit such as a button hole in this sheet portion. The electrocardiogram measurement garment having such a configuration can be released from the electrode portion and the lead wire so that this can be washed conveniently.

International Patent Application Laid-open No. 2017/007016 discloses a wearable electrode provided with a garment having a front fabric and a back fabric, an electrode portion, which is attached to the back fabric opposite to the front fabric, to acquire a biological signal by contact thereof with a subject's body, and a lead wire formed between the front fabric and the back fabric. In that wearable electrode, the electrode portion and the lead wire are freely detachable by a snap button, and a slit is formed in the back fabric of the garment at the position where the electrode is attached. The measurement instrument having the lead wire connected thereto is stored in a pocket formed inside of the garment. Similar to the electrocardiogram measurement garment described in JP '897, the garment of this wearable electrode can be washed as needed because the garment can be released from the electrode portion, the lead wire, and the measurement instrument. In this wearable electrode, the lead wire is arranged between the front fabric and the back fabric of the garment so that discomfort caused by direct contact of the lead wire with the subject's skin can be avoided. Furthermore, that garment is not equipped with a tightening means for bringing the electrode portion into tight contact with the subject's body surface, in which a fiber-structured electrode composed of a nanofiber and an electrically conductive polymer is used as the electrode portion. Because of this, the contact of the electrode portion with the subject's skin can be made more tightly, thereby leading to prevention of the electrode portion from leaving from the subject's skin even when the garment moves due to the subject's body movement so that a stable biological signal can be obtained.

Japanese Patent Application Laid-open No. 2018-153666 discloses a garment provided with an attachment member made of an electrically insulating material, an electrode portion made of an electrically conductive material fixed to the surface of the attachment member in contact with a living body, and a connector electrically connected to the electrode portion. In that garment, the attachment member is fixed to the surface of the garment in contact with the living body. The connector includes an electrically conductive portion for connection to the measurement instrument of a biological signal, and that electrically conductive portion is fixed to the attachment member to expose this electrically conductive portion to the surface opposite to the side of the garment in contact with the living body.

Japanese Patent Application Laid-open No. 2016-179250 discloses a bioelectrical signal monitoring garment provided with a biological signal measurement instrument, two bio-electrodes in contact with a human body, an elastic fabric on which those bioelectrodes are formed, and a detachable connecting member sewn to this elastic fabric. In that bioelectrical signal monitoring garment, it is described that the connecting members are connected to each other under the state that the elastic fabric is stretched. With this, the bioelectrodes are pressed and come into tight contact with the human body so that the quality of the biological signal received by the biological signal measurement instrument can be improved.

International Patent Application Laid-open No. 2018-047814 discloses a biological signal detection garment provided with a garment body portion of a half-top type or a brassiere type, an underbelt having a fastener that allows adjustment of size of the chest circumference and arranged in the lower part of the garment body, two or more electrodes formed of an electrically conductive fiber, a connector to attach a measurement instrument for detection of a biological signal, and a wiring portion for electrically connecting the electrodes to the connector, in which the electrodes, the connector, and the wiring portion are formed in the underbelt. It is described that this biological signal detection garment can detect a biological signal continuously and stably over a long period of time without causing discomfort upon wearing.

However, the electrocardiogram measurement garment described in JP '897 includes a plurality of lead wires fixed with the electrode portion, which may cause problems such as a trouble due to the subject's error in the attachment position of the electrode portion, discomfort caused by the direct contact of the lead wires with the subject's skin, a noise due to the lead wires being pulled by the subject's body movement, a high cost of the lead wires attached with the electrode portion, and a need for an additional fixer for the measurement instrument. In fact, the electrocardiogram measurement garment described in JP '897 was filed more than 25 years ago, but there is no practical product exists.

In the wearable electrodes described in WO '016, the lead wire is disposed between the front fabric and the back fabric so that "the discomfort caused by the direct contact of the lead wire with the subject's skin" can be avoided, and the discomfort having been expected in the electrocardiogram measurement garment described in JP '897 mentioned before. However, the work to insert the lead wire into the garment is time-consuming, and in addition, it is also expected to cause many troubles due to the error in the attachment position of the electrode during this insertion process. Furthermore, with the wearable electrode described in WO '016, it is difficult to provide the garment that perfectly matches the subject's individual size, and when a size of the subject's torso girth is smaller than the standard size of the garment, the force pressing the electrode portion from the garment to the skin becomes weaker and so is the contact between the electrode portion and the skin, thereby making it difficult to obtain a biological signal with a level high enough for the electrocardiogram analysis. On the other hand, when the force of the garment to tight the skin is too strong, an excessive pressure is applied to the subject thereby causing an uncomfortable feeling to the subject.

In the garment provided with the bioelectrode described in JP '666, the electrically insulating member (the attachment member described above) to which the electrode and the electrically conductive portion that connects to the biological signal measurement instrument are fixed is generally composed of a resin or the like, which causes poor moisture absorption and skin feel thereby impairing the comfort of the garment. In addition, when the above garment is washed to remove sweat and dirt, there may be problems such as a damage of the electrically conductive portion and the connector fixed to the garment, the decrease in the electric conductivity, and the disconnect of the wiring. Furthermore, because the electrically conductive member and the electrically insulating member are fixed and processed to the garment, not only the cost of the garment is high, but also the cost of preparing the garment for replacement at the time of washing is a burden for the subject. In addition, the manufacturing process of the garment is also complex. Specifically, various manufacturing processes are required, including the bonding of the electrically insulating member to the fabric of the garment, the attaching process of the electrically conductive portion and the connector, and the quality control in checking the electric conductivity of the electrically conductive portion and the connector after the attachment.

In the bioelectrical signal monitoring garment disclosed in JP '250, an example is shown in which the bioelectrode is in tight contact with a human body by the elastic fabric among the fabrics that constitute the garment. But, in such a configuration, it is difficult for the bioelectrode to be in tight and stable contact with the skin of the human body for a long period of time. In the bioelectrical signal monitoring garment described in JP '250, the area of the garment that includes the location of the bioelectrodes is composed of the elastic fabric so that, if the elastic fabric is stretched to the length shorter than the subject's torso girth and fixed in place as it is, the stretching force of the elastic fabric to press the bioelectrode against the human body may be insufficient. In that instance, the bioelectrode fixed to the elastic fabric will be lifted up from the skin surface of the human body thereby causing a lot of noises in the biological signal. In addition, JP '250 describes that a means to measure a pressure is required to confirm that an appropriate pressure is applied to the bioelectrode, and that it is necessary to have a mechanism for monitoring the pressure to obtain a stable biological signal. Therefore, these can be the causes of the increase in the cost of the garment.

In the biological signal detection garment of a half-top type or a brassiere type described in WO '814, the underbelt to which the electrode and the wiring portion are arranged is formed of an elastic fabric, but this has a structure that surrounds the entire torso girth of the subject. Thus, the adjustment range of the wearing pressure is narrow. Therefore, to adjust the biological signal detection garment to the subject's body shape, it is necessary to prepare many sizes of the garment main body, which leads to a high cost and a difficulty in the inventory management thereof. Furthermore, in the biological signal detection garment described in WO '814, as in JP '666, it is necessary to cover the wiring portion that connects the electrode and the measurement instrument with an electrically insulating member formed of a resin or the like. Accordingly, this causes the problem that the garment is uncomfortable upon wearing. In the biological signal detection garment described in WO '814, also there may be the problem that the electrically conductive portion or the connector can be damaged or disconnected due to washing of the garment. In addition, the high manufacturing cost and the time and efforts required for quality management upon reuse of the garment at a medical institution may be obstacles for widely prevailing use of the garment as a diagnostic device.

As described above, it is concluded that in the known technical field, to monitor the biological signal over a long period of time under a daily living environment, it is desired to develop the biological signal monitoring garment that can be easily washed even when it gets dirty, that can stably measure the biological signal with less noise to the extent that diagnosis of the disease such as the electrocardiogram analysis can be performed, and that can reduce the cost burden to the subject.

It could therefore be helpful to provide at low cost a biological signal monitoring garment that can measure a biological signal comfortably, easily, and stably with a less noise for an intended period of time in the subject engaged in a daily life.

SUMMARY

We thus provide a biological signal monitoring garment including: a plurality of electrodes configured to be in contact with a skin of a subject; an electrically connecting unit configured to electrically connect a biological signal measurement instrument to the electrodes, the biological signal measurement instrument being configured to measure a biological signal of the subject; and a garment main body to which the electrically connecting unit is detachably attached, the garment main body being configured to be worn by the subject. The electrically connecting unit includes: a sheet electrical insulator having flexibility; a plurality of electrode connectors formed on a first surface of both surfaces of the electrical insulator in a thickness direction of the electrical insulator, the electrode connectors being configured to connect the respective electrodes; an instrument connector formed on a second surface of both surfaces of the electrical insulator in the thickness direction, the instrument connector being configured to detachably connect the biological signal measurement instrument, the second surface being a surface on the opposite side of the first surface; and an electrical conductor formed in the electrical insulator, the electrical conductor being configured to electrically connect the electrode connectors to the instrument connector.

The garment main body includes: a torso portion formed annularly around a torso of the subject; an elastic body formed in a back body's torso portion of the torso portion in the garment main body to be longitudinal in a circumferential direction of the torso portion, the elastic body having a length of 30% or more to 60% or less in a longitudinal direction of the elastic body relative to a length of a torso girth in a solar plexus portion of the subject; and a fabric backing sheet having a non-elastic structure and is formed in a front body's torso portion of the torso portion in the garment main body, and the electrically connecting unit is detachably attached to the front body's torso portion where the fabric backing sheet is provided.

A force to expand the elastic body by 30% in the longitude direction of the elastic body is 3 N or more to 9 N or less.

A force to expand the elastic body by 20% in the longitude direction of the elastic body is 2 N or more to 6 N or less.

A rate of an increase in a force required when the elastic body is stretched from 10% expansion to 30% expansion in the longitudinal direction of the elastic body is 0.1 N/% or more to 0.2 N/% or less.

The biological signal monitoring garment further includes a fabric member covering a portion of the first surface of the electrical insulator in the electrically connecting unit other than the electrode connectors.

The biological signal measurement instrument is an electrocardiograph.

The electrodes include an electrically conductive fiber.

The electrodes each are composed of a nanofiber having a fiber diameter of 10 nm or more to 5000 nm or less.

The electrodes each comprise an electrically conductive sheet having an adhesion strength of 200 g/20 mm or less, the adhesion strength being measured with a 90-degree peel-off method in accordance with JIS-Z0237.

There is thus the effect that the biological signal monitoring garment that can comfortably, easily, and stably measure a biological signal with a less noise for an intended period of time in the subject engaged in daily life can be provided at a low cost.

BRIEF DESCRIPTION OF THE DRAWINGS

FIG. 16 is a drawing illustrating one example of electrocardiogram analysis reports obtained in Example 3.

Figure 1:
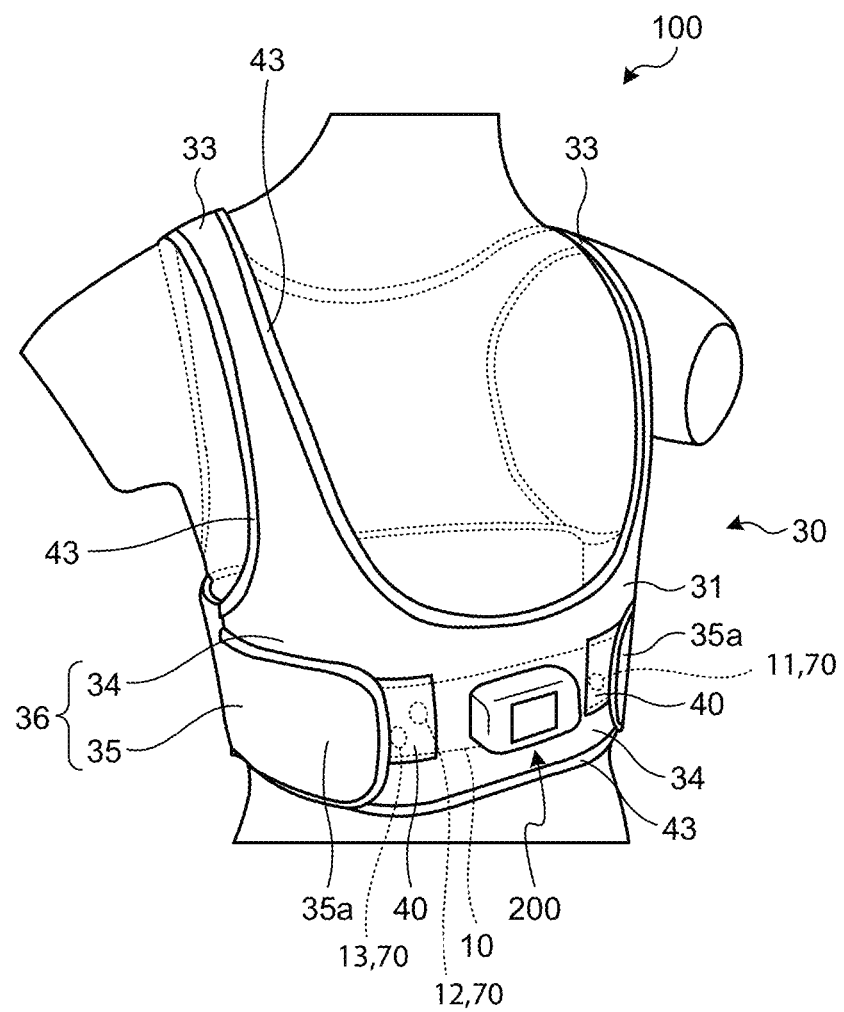
FIG. 1 is a drawing of one composition illustrating a front side of a biological signal monitoring garment according to a first example.

REFERENCE SIGNS LIST 1, 21 Electrical insulator
2a, 2b, 2c, 22a, 22b, 22c Electrode connector
3a, 3b, 3c, 3d, 23a, 23b, 23c, 23d Instrument connector
4a, 4b, 4c, 24a, 24b, 24c Lead wire
5, 6, 26, 27 Fixing portion
10, 10A, 20 Electrically connecting unit
11, 12, 13 Electrode
25 Cover portion
28a, 28b, 28c, 29a, 29b, 29c, 29d Terminal
30, 30A, 30B Garment main body 31, 31A, 31B Front body
32, 32B Back body
32a, 32b Dorsal portion
33, 33A Shoulder strap
34, 35, 36 Torso portion
34a, 35a Side tab
37, 37A Elastic body
38 Fabric backing sheet
39 Unit cover
40, 42 Joint portion
41 Fixing portion
43 Binder tape
51, 52, 53, 54 Instrument connector hole
57, 58, 59 Electrode connector hole
60 Unit storage body
61 Belt loop
62 Loop tape
63 Hook
64 Hook attachment tape
65, 66, 67 Electrode hole
68 Unit loading/unloading port
69 Loop
100, 100A, 100B Biological signal monitoring garment
200 Electrocardiograph
A1 Back surface
A2 Front surface

DETAILED DESCRIPTION

Hereinafter, our biological signal monitoring garment will be described in detail on the basis of the drawings. Our garment is not restricted by the examples. The drawings are schematic and the relationship between the dimensions of each element and the ratio of each element may be different from the real things. There may also be some portions different from each other in dimensional relationships and proportions among these drawings. In the drawings, identical components are tagged with the same symbol.

First Example

Figure 2:
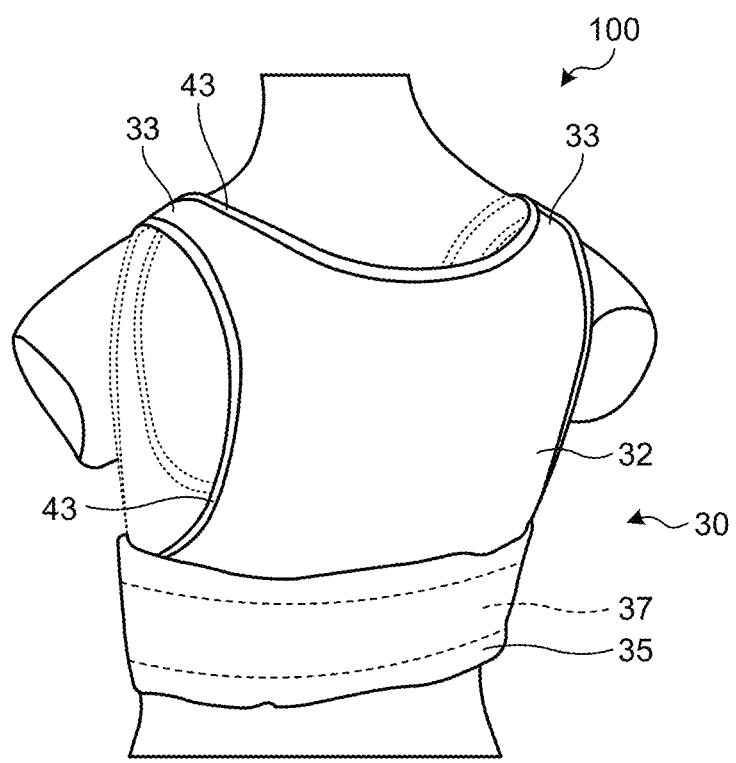
FIG. 2 is a drawing of one composition illustrating a backside of the biological signal monitoring garment according to the first example.

First, a biological signal monitoring garment according to a first example will be described. FIG. 1 is a drawing of one composition illustrating a front side of the biological signal monitoring garment according to the first example. FIG. 2 is a drawing of one composition illustrating a backside of the biological signal monitoring garment according to the first example. FIG. 1 is a drawing of a biological signal monitoring garment 100 according to the first example viewed from a front right oblique direction of a subject who wears this garment. FIG. 2 is a drawing of the biological signal monitoring garment 100 according to the first example viewed from a back left oblique direction of the subject who wears this garment. Hereinafter, the subject means a subject who is subjected to biological signal monitoring, i.e., the subject who wears the biological signal monitoring garment 100 in the first example.

As illustrated in FIGS. 1 and 2, the biological signal monitoring garment 100 according to the first example includes a plurality of electrodes 11 to 13, an electrocardiograph 200, an electrically connecting unit 10 that electrically connects these electrodes 11 to 13 to the electrocardiograph 200, and a garment main body 30 detachably attached with these components and an instrument and is worn by the subject.

The electrodes 11 to 13 are one example of electrodes that come into contact with the subject's skin. As illustrated in FIG. 1, the electrodes 11 to 13 (three in the first example) are arranged on the back surface of the garment main body 30 such that they can be in contact with the subject's skin. Specifically, they are detachably attached to the back surface of the electrically connecting unit 10 arranged on the backside of a torso portion 36 in the garment main body 30. The number of the electrodes 11 to 13 arranged in the biological signal monitoring garment 100 is not limited to three as illustrated in FIG. 1, but this may also be two or more. The arrangement of these electrodes 11 to 13 is not limited to the locations indicated by dashed lines in FIG. 1. For example, the number and arrangement of the electrodes 11 to 13 are determined in accordance with, among other things, the measurement method of the biological signal to be acquired from the subject.

In the biological signal monitoring garment 100 according to the first example, unless otherwise specifically mentioned, the "back surface" means a surface of the skin (body surface) side (the surface facing the skin) of the subject who wears the garment main body 30. The "front surface" means a surface on an opposite side of the "back surface" mentioned above unless otherwise specifically mentioned. The definitions of "back surface" and "front surface" apply to each component of the electrodes 11 to 13, the electrically connecting unit 10, and the garment main body 30 that make up the biological signal monitoring garment 100.

The electrically connecting unit 10 is one example of units that can electrically connect a biological signal measurement instrument (in the first example, the electrocardiograph 200), which measures the subject's biological signal, to the electrodes 11 to 13. As illustrated in FIG. 1, the electrically connecting unit 10 is arranged on the back surface of the garment main body 30. Specifically, the electrically connecting unit 10 is detachably attached to the back surface of a portion corresponding to the subject's abdomen in the torso portion 36 in the garment main body 30. The electrodes 11 to 13 are detachably attached to the back surface of this electrically connecting unit 10. Also, the electrocardiograph 200 is detachably attached to the electrically connecting unit 10 from the front side of the garment main body 30 as illustrated in FIG. 1.

The electrocardiograph 200 is one example of biological signal measurement instruments that measure the subject's biological signals. As illustrated in FIG. 1, the electrocardiograph 200 is detachably attached to the electrically connecting unit 10 from the front side of the torso portion 36 in the garment main body 30, and is electrically connected to the electrodes 11 to 13 through the electrically connecting unit 10. The electrocardiograph 200 has a function to continuously measure the subject's electrocardiogram signal (one example of biological signals) for a period of two weeks or longer without recharging when a battery thereof is charged in advance as well as a function to store the obtained electrocardiogram data (electrocardiogram waveform data from the electrocardiogram signal). It is more preferable that the electrocardiograph 200 have, in addition to these functions, a function to transfer data to a mobile terminal or to a personal computer by communication. This function allows, for example, data to be easily transferred and stored in a personal computer from the electrocardiograph 200 to perform electrocardiogram analysis of the subject on the basis of the stored data.

The garment main body 30 is one example of wears to which the electrically connecting unit 10 is detachably attached and worn by the subject. As illustrated in FIGS. 1 and 2, the garment main body 30 is composed of a front body 31, a back body 32, and shoulder straps 33. Specifically, the front body 31 and the back body 32 are integrally connected to each other by two shoulder straps 33. The front body 31 and the back body 32 are separated at both side portions (corresponding to the flanks of the subject). Both side portions of the front body 31 and the back body 32 are detachably connected as illustrated in FIG. 1.

It is preferable that the front body 31 and the back body 32 be detachably separated at both side portions as described above, but they may also be detachably separated at least at one of both side portions. This makes it easier for the subject to wear the garment main body 30. It is preferable that the front body 31 and the back body 32 be separated at least at one of both side portions, but may be connected at both side portions. It is preferable that the front body 31 and the back body 32 be connected by two shoulder straps 33 as described above, but may be connected by at least one shoulder strap 33. This prevents relative misalignment of the garment main body 30 with the subject under the state that the subject is wearing the garment main body 30.

As illustrated in FIG. 1, the garment main body 30 includes the torso portion 36 that is annular around the subject's torso. In the first example, the torso portion 36 in the garment main body 30 is constructed by connecting a torso portion 34 in the front body 31 to a torso portion 35 in the back body 32. The torso portion 34 in the front body 31 is a portion that extends from the front to the side (flank) of the abdomen of the subject who wears the garment main body 30. On the surface of the torso portion 34 in the front body 31 is formed a joint portion 40 to detachably connect the torso portion 34 in the front body 31 to the torso portion 35 in the back body 32 as illustrated in FIG. 1. Although not illustrated in FIG. 1, a fabric backing sheet with a non-elastic structure is formed by adhering or the like on the back surface of the torso portion 34 of the torso portion 36 in the front body 31 in the garment main body 30. The details of this fabric backing sheet will be described later. The electrically connecting unit 10 is detachably attached to the back surface portion where the fabric backing sheet is formed, in the torso portion 34 of the front body 31. On the other hand, the torso portion 35 in the back body 32 is a portion that extends from the waist to the flank of the subject who wears the garment main body 30. The torso portion 35 in the back body 32 includes a side tab 35a at each end. The torso portion 35 in the back body 32 is connected to the torso portion 34 in the front body 31 by attaching these side tabs 35a to the joint portion 40 of the torso portion 34 in the front body 31. As illustrated in FIGS. 1 and 2, a shrinkable binder tape 43 is sewn around the garment main body 30 to prevent the edges of the cut fabric thereof from unraveling.

As illustrated in FIG. 2, the garment main body 30 includes an elastic body 37 for stretching the torso portion 35 in the back body 32 in accordance with the length of the torso girth of the subject. The elastic body 37 is formed inside the torso portion 35 in the back body 32. The elastic body 37 is stretched by pulling the torso portion 35 in the back body 32 toward the side tabs 35a. When the side tabs 35a are attached to the joint portion 40 of the torso portion 34 in the front body 31 in this stretched state, the elastic body 37 contracts so that the annularly connected torso portion 34 in the front body 31 and the torso portion 35 in the back body 32 (i.e., the torso portion 36 of the garment main body 30) may be brought into tight contact with the subject's body.

In the biological signal monitoring garment 100 according to the first example, the fabric of the garment main body 30, i.e., the fabric of the front body 31, the back body 32, and the shoulder straps 33 constituting the garment main body 30, is preferably a fabric having good stretchability such as a two-way tricot or a smooth knit used for underwear, while more preferably a fabric having, in addition to the stretchability, a sweat-absorbing property and a pleasant feeling upon touching. Illustrative examples of a material for the fabric include polyester type synthetic fibers such as polyethylene terephthalate, polytrimethylene terephthalate, and polybutylene terephthalate as well as polyamide type synthetic fibers such as nylon. In addition, natural materials such as cotton and hemp may also be used as the material for the fabric.

Figure 3A:
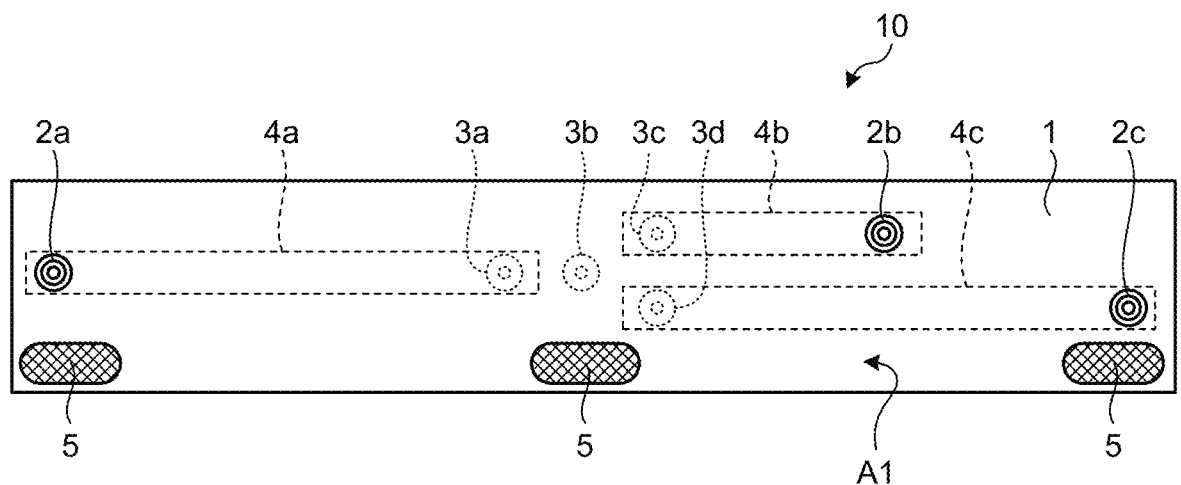
FIG. 3A is a drawing of one composition illustrating an electrode connector side of an electrically connecting unit applied to the biological signal monitoring garment according to the first example.
Figure 3B:
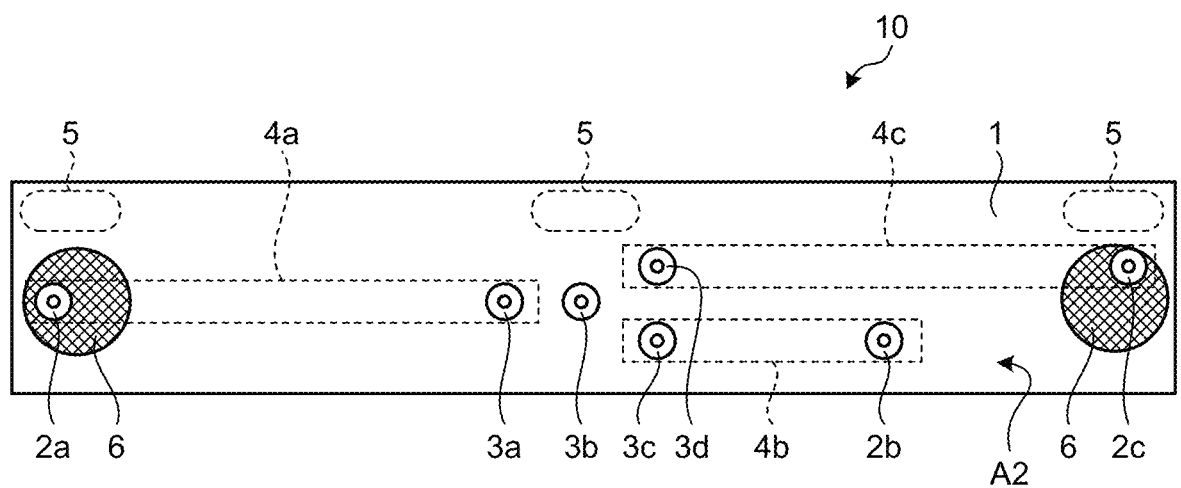
FIG. 3B is a drawing of one composition illustrating an instrument connector side of the electrically connecting unit applied to the biological signal monitoring garment according to the first example.

Next, the electrically connecting unit 10 in the first example will be described. FIG. 3A is a drawing of one composition illustrating an electrode connector side of the electrically connecting unit applied to the biological signal monitoring garment according to the first example. FIG. 3B is a drawing of one composition illustrating an instrument connector side of the electrically connecting unit applied to the biological signal monitoring garment according to the first example. As illustrated in FIGS. 3A and 3B, the electrically connecting unit 10 includes a sheet electrical insulator 1, electrode connectors 2a to 2c, instrument connectors 3a to 3d, and lead wires 4a to 4c. The electrically connecting unit 10 is a unit integrating the electrode connectors 2a to 2c, the instrument connectors 3a to 3d, and the lead wires 4a to 4c into the sheet electrical insulator 1. The electrically connecting unit 10 includes fixing portions 5 and 6 to be detachably attached to the garment main body 30.

The electrical insulator 1 is one example of sheet electrical insulators having flexibility. Specifically, the electrical insulator 1 is constructed by stacking a plurality of electrically insulating sheets. For example, the electrical insulator 1 is formed by overlapping an electrically insulating sheet on the electrode connector side where the electrode connectors 2a to 2c are formed and an electrically insulating sheet on the instrument connector side where the instrument connectors 3a to 3d are formed, followed by bonding these sheets. These two electrically insulating sheets are bonded with each other by the method such as a thermal welding method in which the perimeters of the sheets are adhered using a heat sealer or the like. The electrical insulator 1 is flexible enough to be easily bent in response to an external force, and electrically insulates each of the electrode connectors 2a to 2c, the instrument connectors 3a to 3d, and the lead wires 4a to 4c. As for the electrically insulating material for the electrical insulator 1, for example, a thermoplastic resin such as polyethylene, polypropylene, vinyl chloride resin, polystyrene, or polyamide, or a foamed body of these resins is preferable, and a cross-linked foamed resin is further preferable.

The electrode connectors 2a to 2c are examples of a plurality of electrode connectors each connecting the electrodes 11 to 13 to be in contact with the subject's skin. As illustrated in FIG. 3A, the electrode connectors 2a to 2c (three in the first example) are formed on a first surface (back surface A1) of both surfaces of the electrical insulator 1 in the thickness direction of the electrical insulator 1. For example, these electrode connectors 2a to 2c are formed on the electrically insulating sheet on the electrode connector side and arranged to be exposed from only the back surface A1 during the manufacturing process of the electrical insulator 1. In the first example, the electrode 11 is electrically connected to the electrode connector 2a, the electrode 12 is electrically connected to the electrode connector 2b, and the electrode 13 is electrically connected to the electrode connector 2c. The number and arrangement of the electrode connectors 2a to 2c in the electrical insulator 1 are determined in according with the number and arrangement of the electrodes 11 to 13.

The instrument connectors 3a to 3d are one example of instrument connectors that detachably connect the biological signal measurement instruments. As illustrated in FIG. 3B, the instrument connectors 3a to 3d (four in the first example) are formed on a second surface (front surface A2) of both surfaces of the electrical insulator 1 in the thickness direction of the electrical insulator 1. The second surface is a surface on an opposite side of the first surface (opposite surface). For example, these instrument connectors 3a to 3d are formed on the electrically insulating sheet on the instrument connector side and arranged to be exposed from only the front surface A2 during the manufacturing process of the electrical insulator 1. In the first example, the electrocardiograph 200 (see FIG. 1), which is one example of biological signal measurement instruments, is electrically connected to these instrument connectors 3a to 3d in a detachable fashion. The number and arrangement of the instrument connectors 3a to 3d in the electrical insulator 1 are determined in accordance with the number and arrangement of terminals of the electrocardiograph 200.

As for the electrode connectors 2a to 2c and the instrument connectors 3a to 3d, it is preferable to use, for example, metal dot buttons that have a high corrosion resistance and are applied to devices such as a wearable terminal device and a medical device, and are suitable for measurement of biological signals such as the electrocardiogram signal. The electrode connectors 2a to 2c and the instrument connectors 3a to 3d are not limited to those described above, but may be a connector such as a socket generally used in connection of a cord.

The lead wires 4a to 4c are one example of electrical conductors that electrically connect the electrode connectors 2a to 2c to the instrument connectors 3a to 3d. As illustrated in FIGS. 3A and 3B, the lead wires 4a to 4c (three in the first example) are formed in the electrical insulator 1 to not be exposed from any of the back surface A1 and the front surface A2 of the electrical insulator 1. For example, these lead wires 4a to 4c are formed to be sandwiched between the electrically insulating sheet on the electrode connector side and the electrically insulating sheet on the instrument connector side as described above, and are arranged inside the electrical insulator 1. In the first example, the lead wire 4a electrically connects the electrode connector 2a to the instrument connector 3a, the lead wire 4b electrically connects the electrode connector 2b to the instrument connector 3c, and the lead wire 4c electrically connects the electrode connector 2c to the instrument connector 3d.

It is preferable that the lead wires 4a to 4c be formed by the method in which an electrically conductive resin is printed onto a flexible printing board used in an electronic device or onto a thin electrically insulating resin, or other methods. It is more preferable that the lead wires 4a to 4c be formed by a fiber of an electrically conductive metal wire or the like.

When the lead wires 4a to 4c are made of a fiber having an electric conductivity (sometimes an electrically conductive fiber), this electrically conductive fiber may be a metal-covered yarn in which a polyester fiber or a nylon fiber is covered with a metal fiber such as silver, aluminum, or stainless steel, or a composite fiber in which carbon black is composite-arranged in a part of a core or a shell of polyester or nylon in a longitude direction of the fiber, or a metal-coated yarn in which a polyester fiber or a nylon fiber is coated with a metal such as silver, aluminum, or stainless steel. Among these electrically conductive fibers, from the viewpoint of durability and versatility, the metal-coated yarn is especially preferable. Specifically, a lead wire such as "HITOE (registered trademark) Medical Lead Wire" or "HITOE (registered trademark) Medical Lead Wire II," both being manufactured by Toray Medical Co., Ltd., may be used as the lead wires 4a to 4c.

The fixing portions 5 and 6 are members for realizing detachable attachment of members relating to the electrically connecting unit 10. Specifically, the fixing portion 5 is a member for detachably connecting a cover member that covers the back surface A1 (the surface facing the subject's skin) of the electrically connecting unit 10 in the state that the electrically connecting unit 10 is attached to the back surface of the front body 31 in the garment main body 30. This cover member may be, for example, a unit cover (described later) formed on the back surface of the front body 31. As illustrated in FIG. 3A, a plurality (three in the first example) of the fixing portions 5 is formed on the back surface A1 of the electrically connecting unit 10. For example, these fixing portions 5 are arranged near the lower end of the back surface A1 when the electrically connecting unit 10 is attached to the back surface of the front body 31. As for the fixing portions 5, a member such as a repeatedly usable urethane adhesive sheet or a touch fastener of a surface A (hook surface) or a surface B (loop surface) may be used.

On the other hand, the fixing portion 6 is a member for detachably attaching the electrically connecting unit 10 to the back surface of the front body 31 in the garment main body 30. As illustrated in FIG. 3B, a plurality (two in the first example) of the fixing portions 6 is formed on the front surface A2 of the electrically connecting unit 10. For example, these fixing portions 6 are located near each of right and left ends of the front surface A2 when the electrically connecting unit 10 is attached to the back surface of the front body 31. As for the fixing portions 6, a member such as a repeatedly usable urethane adhesive sheet or a touch fastener of a surface A (hook surface) or a surface B (loop surface) may be used.

Figure 4:
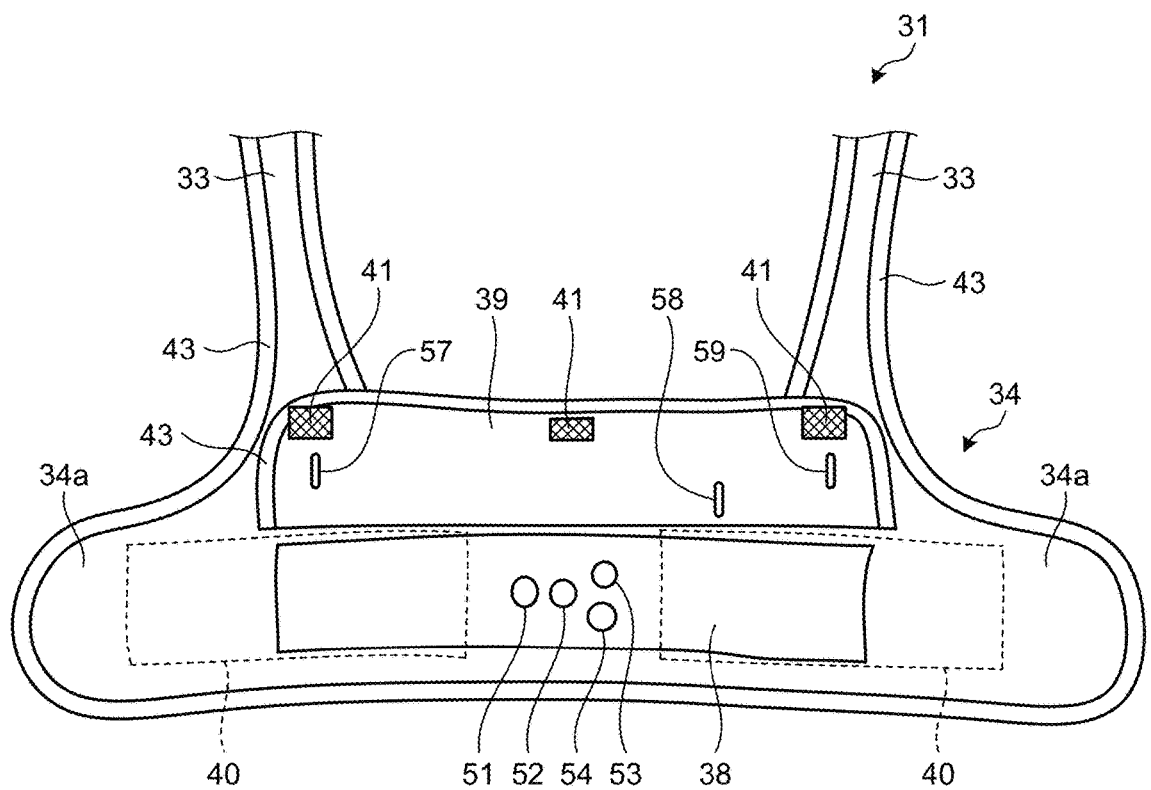
FIG. 4 is a drawing of one composition illustrating a front body in a garment main body according to the first example.

Next, the front body 31 in the garment main body 30 according to the first example will be described. FIG. 4 is a drawing of one composition illustrating the front body of the garment main body according to the first example. FIG. 4 illustrates the front body 31 without attaching the electrically connecting unit 10, viewed from the back side thereof. As illustrated in FIG. 4, the front body 31 includes a fabric backing sheet 38 to which the electrically connecting unit 10 is to be attached, a unit cover 39 that covers the electrically connecting unit 10, and fixing portions 41. The front body 31 also includes side tabs 34a at both ends of the torso portion 34. As with the garment main body 30 described before, the shrinkable binder tape 43 is sewn around the unit cover 39 to prevent the edges of the cut fabric thereof from unraveling.

The fabric backing sheet 38 is one example of fabric backing sheets having a non-elastic structure formed on the portion where the electrically connecting unit 10 can be detachably attached in the torso portion 36 in the garment main body 30 (see FIG. 1). The fabric backing sheet 38 has a non-elastic structure and is bonded to the back surface of the torso portion 34 of the torso portion 36 in the front body 31 in the garment main body 30 as illustrated in FIG. 4. The non-elastic structure of the fabric backing sheet 38 means a structure that has the properties of being difficult to be stretched or non-stretchable, and also has the property of being able to easily bend (such as flexible structure). For example, the fabric backing sheet 38 can be deformed such as bending together with the adhered torso portion 34 in the front body 31, but is less stretchable than the torso portion 34. The fixing portion 6 of the electrically connecting unit 10 illustrated in FIG. 3B is detachably connected to the fabric backing sheet 38 so that the electrically connecting unit 10 is detachably attached to the fabric backing sheet 38. By attaching the electrically connecting unit 10 to the fabric backing sheet 38 in this manner, the fabric backing sheet 38 prevents stretch- or contract-deformation of the torso portion 34 even when the front body 31 stretches or contracts by the movement of the subject or by the action of the elastic body 37 in the back body 32.

For example, a thick adhesive interlining or a touch fastener may also be used as the fabric backing sheet 38. Specifically, when the fabric backing sheet 38 is adhesive interlining, an adhesive member such as a urethane adhesive sheet that can be used repeatedly is used as the fixing portion 6 (see FIG. 3B) attached to the front surface A2 of the electrically connecting unit 10. When the fabric backing sheet 38 is a touch fastener, the touch fastener that can be detachably attached to the touch fastener of the fabric backing sheet 38 is used as the fixing portion 6. In other words, when the fabric backing sheet 38 is the touch fastener with the surface A (hook surface), the fixing portion 6 is the touch fastener with the surface B (loop surface). When the fabric backing sheet 38 is the touch fastener with the surface B (loop surface), the fixing portion 6 is the touch fastener with the surface A (hook surface). In particular, when the touch fastener is used as the fabric backing sheet 38, it is preferable to use the touch fastener with the surface B (loop surface) from the viewpoint of alleviating the discomfort caused by contact with the subject's skin, because the fabric backing sheet 38 faces the skin.

As illustrated in FIG. 4, there is a plurality (e.g., four) of instrument connector holes 51 to 54 in the torso portion 34 and the fabric backing sheet 38 in the front body 31. These instrument connector holes 51 to 54 are through holes for exposing the instrument connectors 3a to 3d (see FIG. 3B) of the electrically connecting unit 10 from the fabric backing sheet 38 side to the front surface side of the front body 31 when the electrically connecting unit 10 is attached to the fabric backing sheet 38. Specifically, after aligning the instrument connectors 3a to 3d and the instrument connector holes 51 to 54 such that they may align with each other, the fixing portion 6 of the electrically connecting unit 10 is connected to the fabric backing sheet 38 so that the electrically connecting unit 10 is detachably attached to the fabric backing sheet 38. At this time, the instrument connector 3a is exposed from the instrument connector hole 51 to the front surface side of the front body 31, and the instrument connector 3b is exposed from the instrument connector hole 52 to the front surface side of the front body 31. Similarly, the instrument connector 3c is exposed from the instrument connector hole 53 to the front surface side of the front body 31, and the instrument connector 3d is exposed from the instrument connector hole 54 to the front surface side of the front body 31. The number and arrangement of these instrument connector holes 51 to 54 are determined in accordance with the number and arrangement of the instrument connectors 3a to 3d formed in the electrically connecting unit 10.

On the other hand, the front surface of the torso portion 34 in the front body 31 is provided with the joint portion 40. As illustrated in FIG. 4, for example, the joint portion 40 is formed by sewing or the like on the surface of the torso portion 34 in the front body 31 at a location spaced from the instrument connector holes 51 to 54 to the side tabs 34a.

This ensures that the joint portion 40 is configured not to cover the instrument connector holes 51 to 54.

The unit cover 39 is one example of fabric members covering a portion of the back surface A1 (first surface) of the electrical insulator 1 in the electrically connecting unit 10 other than the electrode connectors 2a to 2c (see FIG. 3A). As illustrated in FIG. 4, the unit cover 39 is sewn to the back surface of the torso portion 34 in the front body 31 such that this can open and close the portion where the electrically connecting unit 10 is attached in the back surface of the front body 31 (specifically, the portion to which the fabric backing sheet 38 is adhered).

As illustrated in FIG. 4, the unit cover 39 includes a fixing portion 41 and electrode connector holes 57 to 59. The fixing portion 41 is a member for detachably connecting the unit cover 39 to the electrically connecting unit 10 attached to the back surface of the front body 31 in the garment main body 30. Specifically as illustrated in FIG. 4, a plurality (three in the first example) of the fixing portions 41 is formed on the unit cover 39. The number and arrangement of the fixing portion 41 are determined in accordance with the number and arrangement of the fixing portion 5 (see FIG. 3A) attached to the back surface A1 of the electrically connecting unit 10. As for the fixing portion 41, for example, a member such as a touch fastener with a surface A (hook surface) or with a surface B (loop surface) may be used. For example, when the fixing portion 5 in the electrically connecting unit 10 is the touch fastener with the surface A (hook surface), the fixing portion 5 of the electrically connecting unit 10 is the touch fastener with the surface B (loop surface). When the fixing portion 5 in the electrically connecting unit 10 is the touch fastener with the surface B (loop surface), the fixing portion 5 of the electrically connecting unit 10 is the touch fastener with the surface A (hook surface).

The electrode connector holes 57 to 59 are through holes that can expose the electrode connectors 2a to 2c (see FIG. 3A) in the electrically connecting unit 10 attached to the fabric backing sheet 38 from the unit cover 39. Specifically, the electrode connector hole 57 exposes the electrode connector 2a from the unit cover 39. The electrode connector hole 58 exposes the electrode connector 2b from the unit cover 39. The electrode connector hole 59 exposes the electrode connector 2c from the unit cover 39. The number and arrangement of these electrode connector holes 57 to 59 are determined in accordance with the number and arrangement of the electrode connectors 2a to 2c formed in the electrically connecting unit 10.

Figure 5:
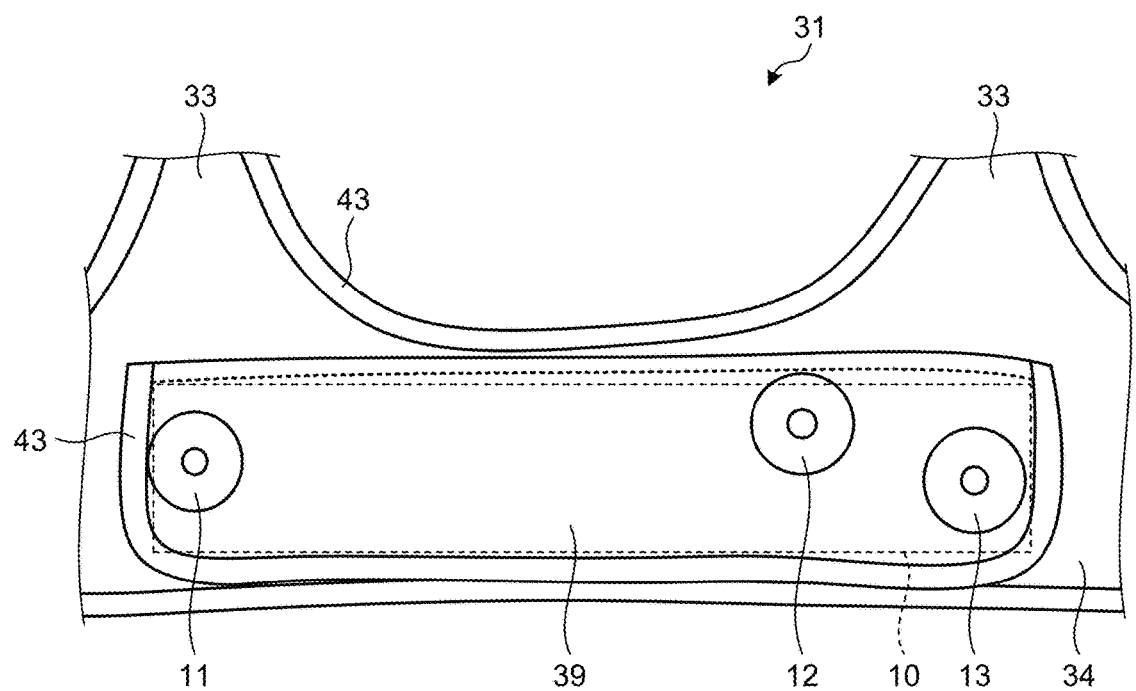
FIG. 5 is a drawing of one composition illustrating a front body under the state of being attached with the electrically connecting unit according to the first example.

FIG. 5 is a drawing of one composition illustrating the front body under the state of being attached with the electrically connecting unit according to the first example. As illustrated in FIGS. 4 and 5, the unit cover 39 closes the electrically connecting unit 10 attached to the fabric backing sheet 38, and thereby covering the back surface A1 of the electrically connecting unit 10 other than the electrode connectors 2a to 2c. At this time, the fixing portions 41 of the unit cover 39 are detachably connected to the fixing portions 5 formed on the back surface A1 of the electrically connecting unit 10. The unit cover 39 covers the electrically connecting unit 10 in the way as described above so that it is possible to prevent the electrically connecting unit 10 from contacting with the subject's skin. The unit cover 39 does not only cover the back surface A1 of the electrically connecting unit 10 as described above, but also supports the electrically connecting unit 10 between this and the fabric backing sheet 38. By so doing, the unit cover 39 can prevent not only the electrically connecting unit 10 from being misaligned with the fabric backing sheet 38 but also the electrically connecting unit 10 from falling from the torso portion 34 in the front body 31.

As illustrated in FIG. 5, the electrodes 11 to 13 in contact with the subject's skin are electrically connected to the electrically connecting unit 10, which is under the state of being covered by the unit cover 39. Specifically, the electrode 11 is detachably connected to the electrode connector 2a in the electrically connecting unit 10 through the electrode connector hole 57 in the unit cover 39. The electrode 12 is detachably connected to the electrode connector 2b in the electrically connecting unit 10 through the electrode connector hole 58 in the unit cover 39. The electrode 13 is detachably connected to the electrode connector 2c in the electrically connecting unit 10 through the electrode connector hole 59 in the unit cover 39. In the first example, the electrodes 11 to 13 are arranged in accordance with CC5, which is one of the induction methods of the Holter electrocardiography. At this time, the electrode 11 is a positive electrode, the electrode 12 is a ground electrode, and the electrode 13 is a negative electrode.

In the biological signal monitoring garment 100 according to the first example, the electrodes 11 to 13, which detect the biological signal such as the electrocardiogram signal from the subject's body, are, for example, structural bodies formed of an electrically conductive fiber (i.e., electrically conductive fiber structural body). The electrically conductive fiber is preferably a fiber impregnated with an electrically conductive substance. More preferably, the electrically conductive fiber structural body is made of multi-filaments, and an electrically conductive polymer is supported onto the surfaces of monofilaments as well as in the space formed between the monofilaments, which constitute this electrically conductive fiber structural body.

There is no particular restriction in the electrically conductive substance to be used in the electrodes 11 to 13 as far as this substance is a compound having an electric conductivity. Illustrative examples of the electrically conductive substance include electrically conductive polymers such as PEDOT/PSS and an electrically conductive substance blended with carbon black, CNT (carbon nanotube), and metal particulate. When a substance having an elastic property such as an elastomer resin is used as the electrically conductive substance, the electric conductivity changes depending on the elastic condition of the substance. Thus, stable detection of the biological signal from the subject is difficult. Therefore, the substance having the elasticity is not suitable as the electrically conductive substance. The electrically conductive polymer to be used for the electrodes 11 to 13 described above is an electrically conductive polymer that a resin itself is electrically conductive. In view of safety and processability, for example, the electrically conductive polymer is more preferably PEDOT/PSS in which a thiophene-type electrically conductive polymer PEDOT is doped with polystyrene sulfonic acid (poly(4-styrene sulfonate) (PSS)). When carbon black, CNT, or metal particulate is used as the electrically conductive substance, a polymer such as a urethane-type polycarbonate or a urethane-type polyether may be used as the binder.

Illustrative examples of the form of the electrically conductive fiber structural body to be used for the electrodes 11 to 13 include: textile bodies such as a knitted body, a woven body, and an unwoven cloth; and a strap body. Among these, a knitted body or a woven body is preferably used.

Fiber materials for the electrically conductive fiber structural body are synthetic fibers and the like. Illustrative examples of the synthetic fiber include: fibers formed of polyethylene terephthalate, polypropylene terephthalate, or polybutylene terephthalate; aromatic polyester type fibers formed by copolymerizing these polymers with a third component; aliphatic polyester type fibers represented by those formed of L-lactic acid as a main component therein; polyamide type fibers such as nylon 6 and nylon 66; acrylic fibers formed of polyacrylonitrile as a main component therein; polyolefin type fibers such as polyethylene and polypropylene; and polyvinyl chloride type fibers. In addition, a fiber blended with an additive such as titanium oxide, and a fiber having a polymer reformed to be provided with functionality such as an enhanced moisture-absorption property may also be used as the fiber materials.

From the viewpoint to support the electrically conductive resin onto a fiber surface and into a space formed between fibers, it is preferable that the electrically conductive fiber structural body include multi-filaments whose monofilament fiber diameter is 0.2 dtex or less. The mixing rate of the multi-filaments whose monofilament fiber diameter is 0.2 dtex or less in the fiber structural body is not particularly restricted as far as the performance thereof is not affected. In view of electric conductivity and durability, preferably the mixing rate is higher, and more preferably the mixing rate is in the range of 50% or higher to 100% or less. Also, the more the number of the monofilament is, the more the electrically conductive resin is supported in the fiber structural body because the space formed of a plurality of the monofilaments (i.e., a portion in which the electrically conductive resin is supported) is subdivided. Moreover, the finer the fiber diameter becomes, the more the continuity of the electrically conductive resin is maintained even when the space is subdivided. Therefore, when the number and the fiber diameter of monofilaments meet the above conditions, the electrically conductive fiber structure having excellent high-electric conductivity and washing durability can be obtained. When the electrodes 11 to 13 are made of the fiber structural body impregnated with an electrically conductive material, it is preferable that these electrodes 11 to 13 be composed of microfibers having a fiber diameter of 5 m or less, like the fiber structural body used in an artificial leather, an outer material, or the like. In particular, it is more preferable that these electrodes 11 to 13 be composed of nanofibers having a fiber diameter of 10 nm or more to 5000 nm or less.

The fiber structural body including nanofibers produced by a known method such as a nanofiber staple yarn aggregate produced from "Nanoalloy (registered trade mark)" fiber and a monofilament yarn aggregate produced by an electrospinning method, may be preferably used as the nanofiber that constitutes the electrodes 11 to 13. The fiber structural body containing multifilament yarns of the nanofibers is particularly preferable for this fiber structural body. The nanofiber multifilament yarn may be produced by a known conjugate spinning method or the like. For example, among others, a nanofiber multifilament yarn having a small fluctuation in the fiber diameter obtained by removing a sea portion of a conjugate fiber using a conjugate spinneret may be effectively used as illustrated in Japanese Patent Application Laid-open No. 2013-185283, but this disclosure is not limited to them.

The electrodes 11 to 13 described above are not limited to those made of the electrically conductive fiber, but may also be those provided with an electrically conductive sheet such as an adhesive film containing an electrically conductive substance. In this example, it is preferable that the electrically conductive sheet that constitute each of the electrodes 11 to 13 have an adhesion strength of 200 g/20 mm or less as measured by the 90-degree peeling method in accordance with JIS-Z0237.

The size and shape of the electrodes 11 to 13 are not particularly specified as far as the biological signal can be detected. For example, the length and width of these electrodes 11 to 13 are preferably 2.0 cm or more to 5.0 cm or less. Specifically, illustrative examples of the electrodes 11 to 13 that can be used include "HITOE (registered trademark) Medical Electrode" and "HITOE (registered trademark) Medical Electrode II," manufactured by Toray Medical Co., Ltd.

On the other hand, the side tab 34a in the front body 31 as illustrated in FIG. 4 is a portion corresponding to the subject's flank and is connected to the torso portion 35 in the back body 32 to be overlapped with each other. At this time, the torso portion 35 in the back body 32 is detachably connected to the joint portion 40 formed on the front surface of the front body 31. As a result, the torso portion 34 in the front body 31 and the torso portion 35 in the back body 32 are annularly connected to form the torso portion 36 in the garment main body 30 (see FIG. 1).

Figure 6:
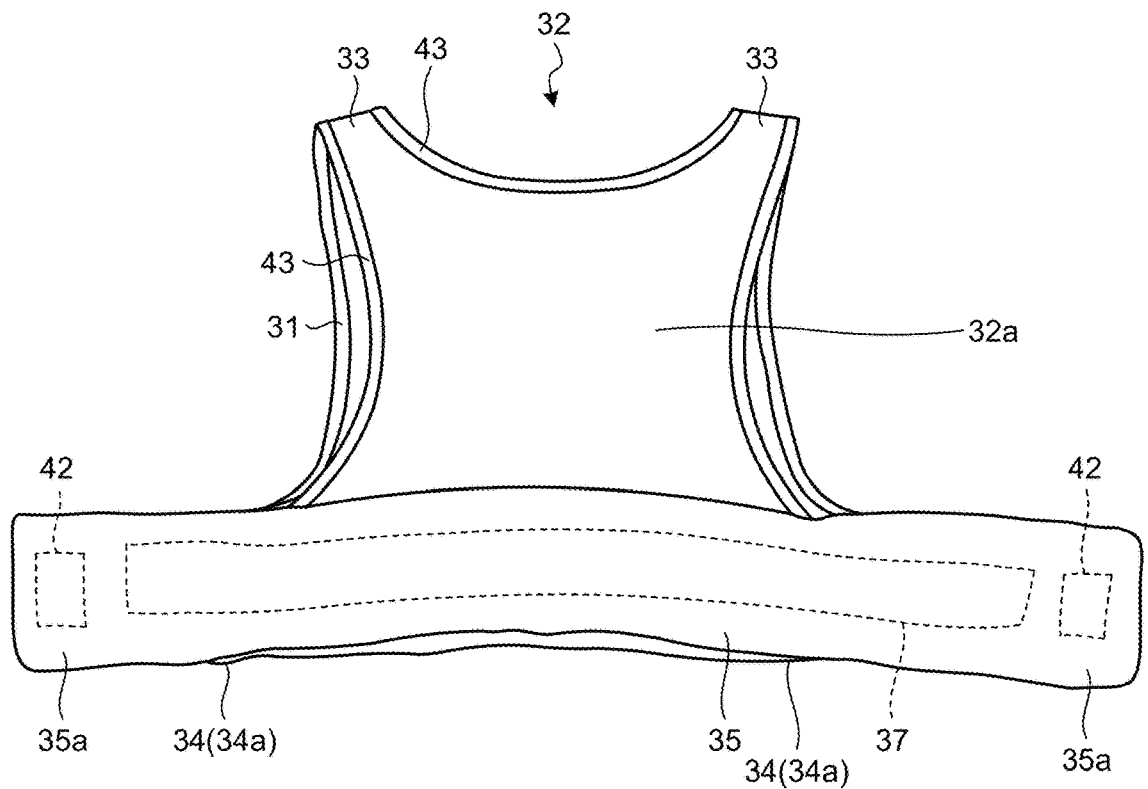
FIG. 6 is a drawing of one composition illustrating a back body in the garment main body according to the first example.

Next, the back body 32 of the garment main body 30 according to the first example will be described. FIG. 6 is a drawing of one composition illustrating the back body of the garment main body according to the first example. As illustrated in FIG. 6, the back body 32 includes a dorsal portion 32a, the torso portion 35, the elastic body 37, and a joint portion 42. The back body 32 includes the side tabs 35a at both ends of the torso portion 35.

The dorsal portion 32a is a portion corresponding to the back of the subject who wears the garment main body 30. As illustrated in FIG. 6, the dorsal portion 32a is integrally connected to the front body 31 by one or more (two in the first example) shoulder straps 33. The lower end of the dorsal portion 32a (the end opposite to the shoulder strap 33) includes the torso portion 35.

The torso portion 35 is connected to the torso portion 34 of the front body 31 to form the torso portion 36 of the garment main body 30 (see FIGS. 1 and 2) annularly around the subject's torso. As illustrated in FIG. 6, the torso portion 35 is band-shaped and located at the lower end of the dorsal portion 32a. The torso portion 35 is formed, for example, as a stretchable, hollow band and includes the elastic body 37 inside thereof. The torso portion 35, which is band-shaped, includes the side tabs 35a at both ends thereof and the joint portion 42 on the back surface of the side tabs 35a.

The elastic body 37 provides elasticity (stretching force) to the torso portion 35 in the back body 32, which is stretchable in the longitudinal direction of the band. The elastic body 37 is formed in the torso portion 36 to be longitudinal in the circumferential direction of the torso portion 36 that forms an annularity in the garment main body 30 as illustrated in FIG. 2. Specifically, as illustrated in FIG. 6, the elastic body 37 is incorporated into the torso portion 35 of the band-shaped torso portion 36 in the back body 32 to be longitudinal in the longitudinal direction of the torso portion 35. The length of the elastic body 37 is in the range of 30% or more to 60% or less relative to the length of the torso girth in the longitudinal direction in the subject's solar plexus portion. By setting the longitudinal length of the elastic body 37 to the above length, the electrodes 11 to 13 (see FIG. 5) attached to the back surface of the garment main body 30 can be brought into contact with the subject's skin with an appropriate pressure. As a result, the biological signal can be acquired from the subject through the electrodes 11 to 13 without giving the subject a sense of an excessively high pressure due to wearing of the garment main body 30. It is preferable that the elastic body 37 have a length (width) of 25 mm or more to 50 mm or less in the direction perpendicular to the longitudinal direction thereof. Furthermore, it is preferable that the elastic body 37 do not change over a long time in the stress and strain characteristics thereof. According to the first example, for example, a flat rubber having a width of 40 mm is used as the elastic body 37. Polyurethane, a natural rubber or the like is used as a material for the elastic body 37.

The force to expand the elastic body 37 by 30% in the longitude direction thereof (30%-expansion force) is preferably 3 N or more to 9 N or less. When the 30%-expansion force of the elastic body 37 is less than 3 N, the pressure to the subject's skin is so low that there may be an unintended release of the contact of the subject's skin to the electrodes 11 to 13 thereby bringing about a risk that it may be difficult to obtain the biological signal. When the 30%-expansion force of the elastic body 37 is greater than 9 N, the compression force may be felt too strong by the subject when wearing the garment main body 30. Hence, the comfort of wearing the garment main body 30 is lost, resulting in the deterioration of the wearing comfort of the garment main body 30. The force to expand the elastic body 37 by 20% in the longitude direction thereof (20%-expansion force) is preferably 2 N or more to 6 N or less.

The rate of the increase in the force required when the elastic body 37 is expanded from 10% expansion to 30% expansion in the longitudinal direction thereof is preferably 0.1 N/% or more to 0.2 N/% or less. Illustrative examples of the elastic body 37 described above include LY-40, manufactured by Kitani Co., Ltd.

The joint portion 42 is a member for connecting the torso portion 35 in the back body 32 to the torso portion 34 in the front body 31. The joint portion 42 is composed of a detachable adhesive member such as a touch fastener, in which this is formed by sewing the member to the back surface of the torso portion 35 in the back body 32 (specifically, to the back surface of the side tab 35a in the torso portion 35) as illustrated in FIG. 6. The joint portion 42 is detachably connected to the joint portion 40 (see FIG. 1) formed on the front surface of the torso portion 34 in the front body 31. Specifically, when the joint portion 42 in the back body 32 is the touch fastener with the surface A (hook surface), the joint portion 40 in the front body 31 is the touch fastener with the surface B (loop surface). When the joint portion 42 in the back body 32 is the touch fastener with the surface B (loop surface), the joint portion 40 in the front body 31 is the touch fastener with the surface A (hook surface). By connection of the joint portions 40 and 42 with each other, the torso portion 35 in the back body 32 is connected to the torso portion 34 in the front body 31 to form an annularity around the subject's torso.

The torso portion 35 in the back body 32 is stretched together with the elastic body 37 according to the length of the torso girth such as the subject's abdominal circumference, and is annularly connected to the torso portion 34 in the front body 31 by connection of the joint portions 40 and 42 with each other. In other words, the joint portion 42 in the back body 32 and the joint portion 40 in the front body 31 function as size adjustment functional portions that allow the circumferential size of the torso portion 36 of the garment main body 30 to be adjusted according to the length of the subject's torso.

As described above, according to the first example, the electrode connectors 2a to 2c, the instrument connectors 3a to 3d, and the lead wires 4a to 4c are integrated into the sheet electrical insulator 1 to form the electrically connecting unit 10, which is flexible and bendable so that the electrically connecting unit 10 is detachably attached to the garment main body 30 worn by the subject, and also, the electrodes 11 to 13 to be in contact with the subject's skin and the biological signal measurement instrument (for example, electrocardiograph 200) to measure the subject's biological signal are each detachably attached to the electrode connectors 2a to 2c and the instrument connectors 3a to 3d of the electrically connecting unit 10.

By so doing, conduction wiring between the electrodes 11 to 13 and the biological signal measurement instrument can be formed without an error so that the biological signal monitoring garment 100 can be conveniently prepared by attaching the electrically connecting unit 10, the electrodes 11 to 13, and the biological signal measurement instrument to the garment main body 30. When the subject wears the biological signal monitoring garment 100, in accordance with the subject's movement, the electrically connecting unit 10 can be flexibly deformed, and also the contact of the electrodes 11 to 13 with the subject's skin can be retained. As a result, the subject's feeling of wrongness and discomfort due to the electrically connecting unit 10 can be alleviated, thereby making the biological signal monitoring garment 100 comfortable upon wearing, while at the same time allowing the subject engaged in a daily life to conveniently continue to measure the biological signal stably with less noise to the extent that diagnosis of a disease such as the electrocardiogram analysis can be performed over a long period of time such as one week or longer without forcing an excessive tensile stress to the lead wires 4a to 4c in the electrically connecting unit 10.

In addition, even when the garment main body 30 is replaced due to sweat or dirt, the subject himself can easily detach the electrically connecting unit 10, the electrodes 11 to 13, and the biological signal measurement instrument from the garment main body 30. This allows the subject to wear the biological signal monitoring garment 100 having been replaced with a clean garment main body 30 and wash the garment main body 30 having been taken off. As a result, the biological signal can be measured comfortably for the subject under the clean condition of the biological signal monitoring garment 100.

Furthermore, because the electrically connecting unit 10, the electrodes 11 to 13, and the biological signal measurement instrument can be easily attached to and detached from the garment main body 30, not only the cost required for manufacturing the biological signal monitoring garment 100 can be reduced compared to those in which the components such as the wiring and the electrodes are fixed to the garment, but also the cost required for preparation of the garment main body 30 for replacement can be reduced. Accordingly, the biological signal monitoring garment 100 can be provided inexpensively to many subjects.

In the first example, the elastic body 37 is formed in the torso portion 36 in the garment main body 30 so that the torso portion 36 can be stretched and contracted together with the elastic body 37 in the subject's torso circumference direction. This allows the torso portion 36 in the garment main body 30 to freely stretch and contract in accordance with various body shapes, sizes, or movements of subjects engaged in daily activities, including walking, as well as ascending and descending the stairs. This allows the subject's torso to be tightened with a moderate pressure by the torso portion 36 in the garment main body 30 so that the contact state of the subject's skin with the electrodes 11 to 13 can be easily retained.

Second Example

Figure 7:
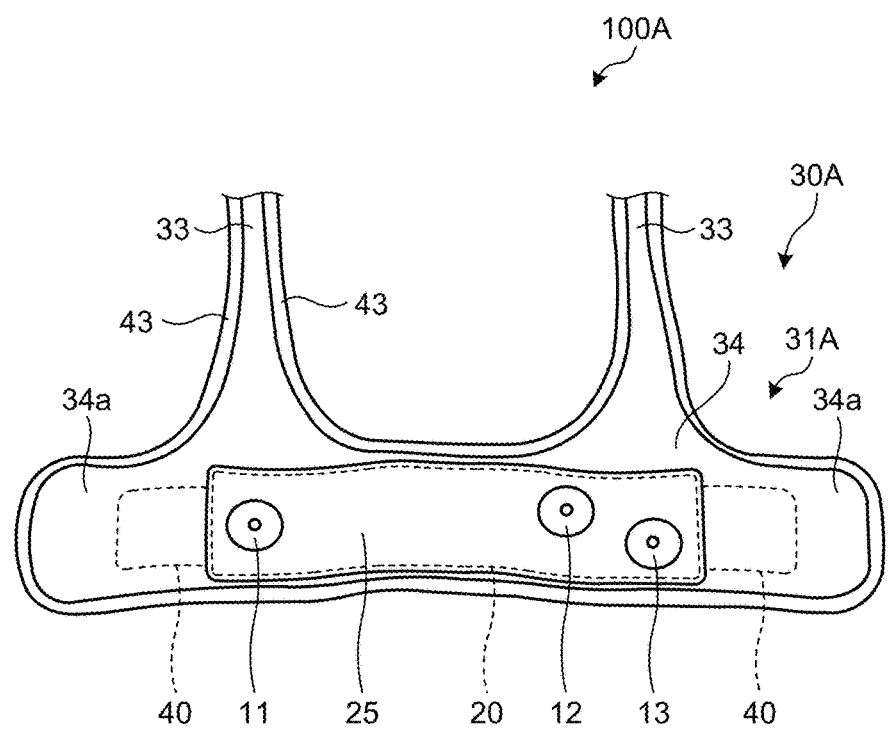
FIG. 7 is a drawing of one composition illustrating a biological signal monitoring garment according to a second example.

Next, a biological signal monitoring garment according to a second example will be described. FIG. 7 is a drawing of one composition illustrating the biological signal monitoring garment according to the second example. FIG. 7 illustrates a front body 31A of a garment main body 30A, which is one composition portion of a biological signal monitoring garment 100A according to the second example, viewed from the back surface thereof. As illustrated in FIG. 7, the biological signal monitoring garment 100A according to the second example includes the garment main body 30A in place of the garment main body 30 of the biological signal monitoring garment 100 according to the first example described above, and an electrically connecting unit 20 in place of the electrically connecting unit 10. The garment main body 30A includes the front body 31A in place of the front body 31 in the garment main body 30 in the first example. Other components are the same as those in the first example, and the same tags are attached to the same components. In the second example, a subject means a subject who wears the biological signal monitoring garment 100A according to the second example.

As illustrated in FIG. 7, the electrically connecting unit 20 having a cover portion 25 is detachably attached to the back surface of the torso portion 34 in the front body 31A. As in the first example, the electrodes 11 to 13 to be in contact with the subject's skin are detachably attached to the electrically connecting unit 20. Although not specifically illustrated in FIG. 7, the electrocardiograph 200 (see FIG. 1), which is one example of biological signal measuring instruments, is detachably attached to the front surface of the front body 31A to be connected to the electrodes 11 to 13 through the electrically connecting unit 20, as in the first example. The front body 31A is integrally connected to the back body 32 (see FIG. 2) by two shoulder straps 33.

Figure 8A:
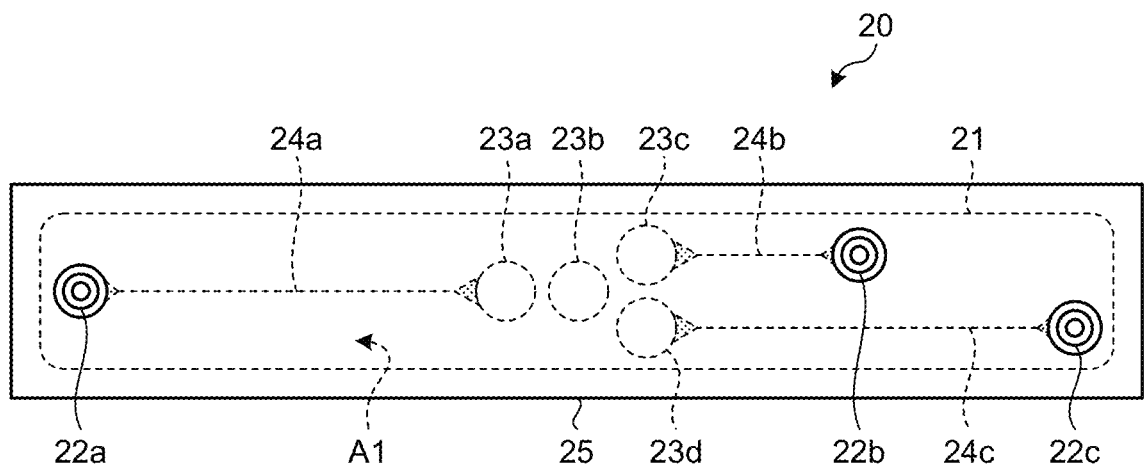
FIG. 8A is a drawing of one composition illustrating an electrode connector side of an electrically connecting unit applied to the biological signal monitoring garment according to the second example.
Figure 8B:
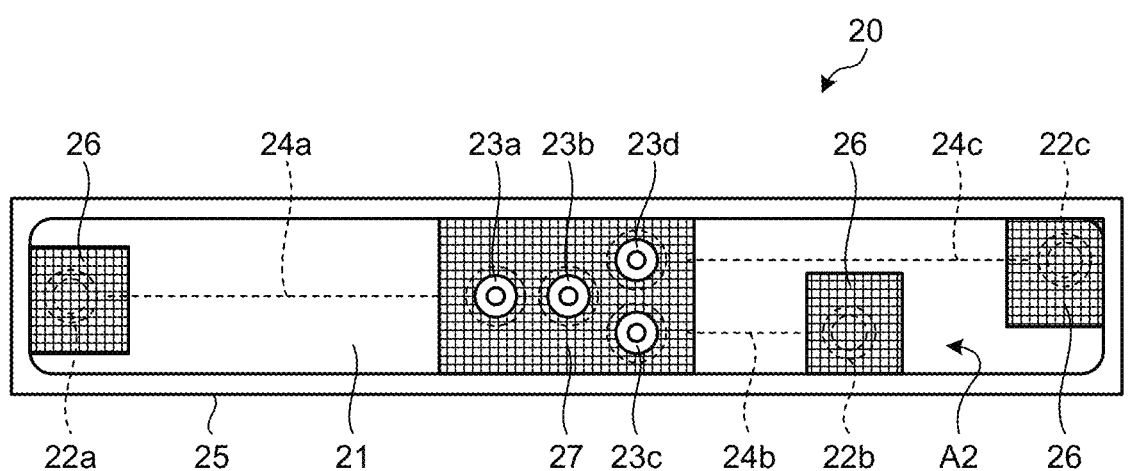
FIG. 8B is a drawing of one composition illustrating an instrument connector side of the electrically connecting unit applied to the biological signal monitoring garment according to the second example.

FIG. 8A is a drawing of one composition illustrating the electrode connector side of the electrically connecting unit applied to the biological signal monitoring garment according to the second example. FIG. 8B is a drawing of one composition illustrating the instrument connector side of the electrically connecting unit applied to the biological signal monitoring garment according to the second example. As illustrated in FIGS. 8A and 8B, the electrically connecting unit 20 includes a sheet electrical insulator 21, electrode connectors 22a to 22c, instrument connectors 23a to 23d, lead wires 24a to 24c, and the cover portion 25. The electrically connecting unit 20 is a unit integrating the electrode connectors 22a to 22c, the instrument connectors 23a to 23d, and the lead wires 24a to 24c into the sheet electrical insulator 21. The electrically connecting unit 20 includes fixing portions 26 and 27 to be detachably attached to the garment main body 30A.

Figure 9:
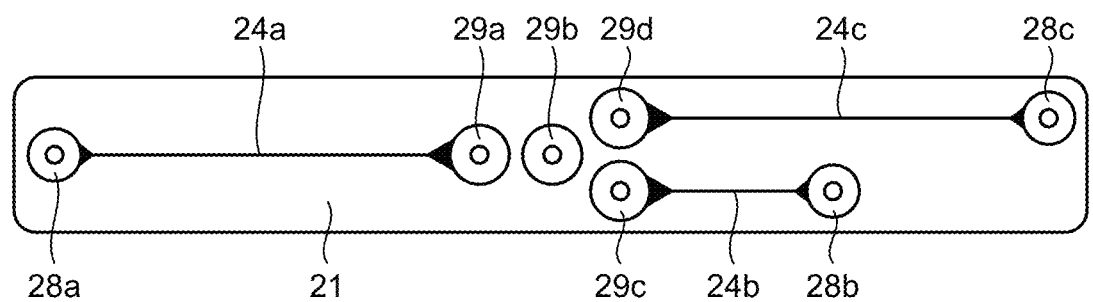
FIG. 9 is a drawing of one composition illustrating a sheet electrical insulator applied to the electrically connecting unit according to the second example.

The electrical insulator 21 is one example of flexible sheet electrical insulators. FIG. 9 is a drawing of one composition illustrating the sheet electrical insulator applied to the electrically connecting unit according to the second example. In the second example, the electrical insulator 21 is configured to be a flexible and bendable sheet form by a flexible electrically insulating board or the like. The lead wires 24a to 24c and terminals 28a to 28c and 29a to 29d are formed in the electrical insulator 21 as illustrated in FIG. 9. For example, the lead wire 24a is formed to electrically connect the terminal 28a to the terminal 29a. The lead wire 24b is formed to electrically connect the terminal 28b to the terminal 29c. The lead wire 24c is formed to electrically connect the terminal 28c to the terminal 29d. The terminals 28a to 28c are terminals for electrically connecting the electrode connectors 22a to 22c, respectively. On the other hand, the terminals 29a to 29d are terminals for electrically connecting the instrument connectors 23a to 23d, respectively. The electrical insulator 21 is fabricated using a polyester film as the base film board by forming an electrically insulating protective film on this base film board to protect the lead wires 24a to 24c. This protective film is formed on the board surface of the base film board that constitutes the electrical insulator 21 other than the terminals 28a to 28c and 29a to 29d. The electrical insulator 21 is flexible enough to be bent easily in response to an external force, and electrically insulates among the electrode connectors 22a to 22c, the instrument connectors 23a to 23d, and the lead wires 24a to 24c as illustrated in FIGS. 8A and 8B.

The electrode connectors 22a to 22c are one example of electrode connectors to which the electrodes 11 to 13 to be in contact with the subject's skin are connected. As illustrated in FIG. 8A, the electrode connectors 22a to 22c (three in the second example) are formed, of both surfaces of the electrical insulator 21 in the thickness direction, on the back surface A1. For example, these electrode connectors 22a to 22c are each formed to the terminals 28a to 28c of the electrical insulator 21 as illustrated in FIG. 9, and configured to be exposed from only the back surface A1 of the electrical insulator 21. The electrodes 11 to 13 are electrically and detachably connected to the electrode connectors 22a to 22c, respectively, in the same manner as in the first (see FIG. 7). The number and arrangement of the electrode connectors 22a to 22c in the electrical insulator 21 are determined in according with the number and arrangement of the electrodes 11 to 13.

The instrument connectors 23a to 23d are one example of instrument connectors that detachably connect the biological signal measurement instrument. As illustrated in FIG. 8B, a plurality (four in the second example) of the instrument connectors 23a to 23d are formed, of both surfaces of the electrical insulator 21 in the thickness direction, on a surface A2. For example, the instrument connectors 23a to 23d are each formed to the terminals 29a to 29d of the electrical insulator 21 as illustrated in FIG. 9, and are configured to be exposed only from the surface A2 of the electrical insulator 21. As in the first example, the electrocardiograph 200 (see FIG. 1), which is one example of biological signal measurement instruments, is electrically and detachably connected to the instrument connectors 23a to 23d. The number and arrangement of the instrument connectors 23a to 23d in the electrical insulator 21 are determined in accordance with the number and arrangement of the terminals of the electrocardiograph 200.

As in the first example, it is preferable to use metal dot buttons having a high corrosion resistance as the electrode connectors 22a to 22c and the instrument connectors 23a to 23d in the second example. The electrode connectors 22a to 22c and the instrument connectors 23a to 23d are not limited to those described above, but may be a connector such as a socket generally used in connection of a cord.

The lead wires 24a to 24c are one example of electrical conductors that electrically connect the electrode connectors 22a to 22c to the instrument connectors 23a to 23d. As illustrated in FIGS. 8A and 8B, the lead wires 24a to 24c (three in the second example) are covered, for example, by the electrical insulator 21, which is a protective film, and are not exposed from any of the back surface A1 and the front surface A2 of the electrical insulator 21. It is preferable that the lead wires 24a to 24c be wired, for example, by printing an electrically conductive resin on the surface of the electrical insulator 21. In the second example, the lead wire 24a electrically connects the electrode connector 22a to the instrument connector 23a, the lead wire 24b electrically connects the electrode connector 22b to the instrument connector 23c, and the lead wire 24c electrically connects the electrode connector 22c to the instrument connector 23d.

The cover portion 25 is a component to avoid the direct contact between the subject's skin and the electrically connecting unit 20. The cover portion 25 is made of, for example, the same fabric material as that of the garment main body 30, and is formed on the first surface (back surface A1) of the electrical insulator 21 in the electrically connecting unit 20. Specifically, as illustrated in FIGS. 8A and 8B, the cover portion 25 is adhered to the back surface A1 of the electrical insulator 21 to cover the portion of the back surface A1 other than the electrode connectors 22a to 22c.

The fixing portions 26 and 27 are members for detachably attaching the electrically connecting unit 20 to the back surface of the front body 31A of the garment main body 30A. For example, as illustrated in FIG. 8B, the fixing portions 26 are each formed on a portion corresponding to the electrode connectors 22a to 22c in the front surface A2 of the electrically connecting unit 20. The fixing portion 27 is formed on a portion corresponding to the instrument connectors 23a to 23d in the front surface A2 of the electrically connecting unit 20. As for the fixing portions 26 and 27, a member such as a repeatedly usable urethane adhesive sheet or a touch fastener with a surface A (hook surface) or with a surface B (loop surface) may be used.

Figure 10:
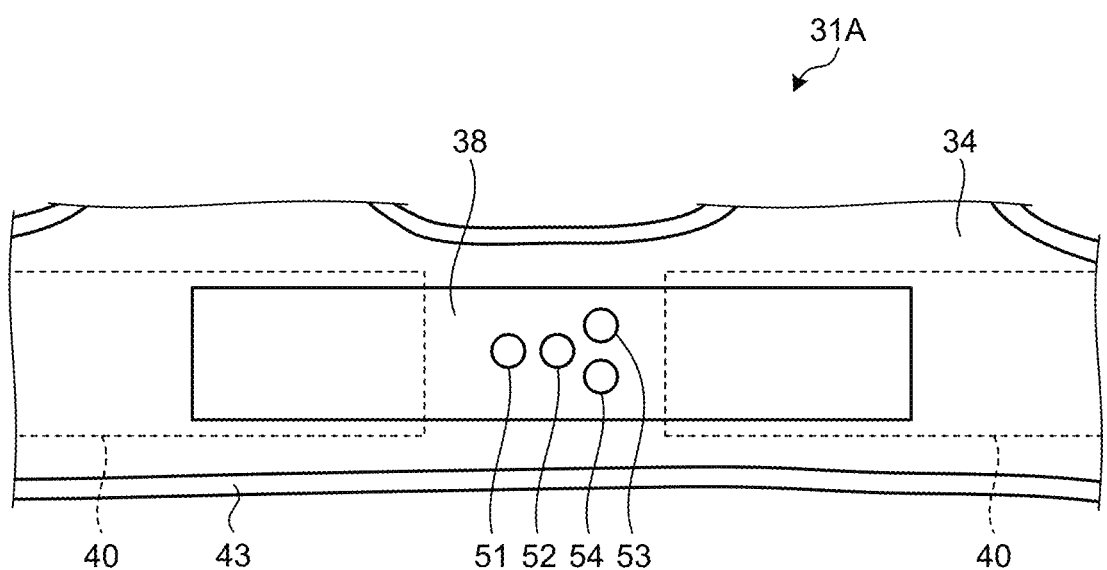
FIG. 10 is a drawing of one composition illustrating a front body in the garment main body according to the second example.

Next, the front body 31A of the garment main body 30A in the second example will be described. FIG. 10 is a drawing of one composition illustrating the front body of the garment main body according to the second example. FIG. 10 illustrates the front body 31A without attaching the electrically connecting unit 20, viewed from the back side thereof. As illustrated in FIG. 10, the front body 31A includes the fabric backing sheet 38, the side tabs 34a, and the joint portions 40 in the torso portion 34, as in the first example. On the other hand, in the second example, the front body 31A is not provided with the unit cover 39 and the fixing portion 41 as in the first example. As exemplified by the front body 31A in FIG. 10, the binder tape 43 is sewn around the garment main body 30A in the second example to prevent the edges of the cut fabric from unraveling, as in the first example.

In the second example, the fixing portions 26 and 27 (see FIG. 8B) in the electrically connecting unit 20 are detachably connected to the fabric backing sheet 38 illustrated in FIG. 10 so that the electrically connecting unit 20 is detachably attached to the fabric backing sheet 38. As for this fabric backing sheet 38, thick adhesive interlining or a touch fastener may be used, as in the first example. Specifically, when the fabric backing sheet 38 is adhesive interlining, an adhesive member such as a urethane adhesive sheet that can be used repeatedly is used as the fixing portions 26 and 27 attached to the surface A2 of the electrically connecting unit 20. When the fabric backing sheet 38 is a touch fastener, the touch fastener that can be detachably attached to the touch fastener of the fabric backing sheet 38 is used as the fixing portions 26 and 27. In other words, when the fabric backing sheet 38 is a touch fastener with a surface A (hook surface), the fixing portions 26 and 27 are a touch fastener with a surface B (loop surface). When the fabric backing sheet 38 is a touch fastener with a surface B (loop surface), the fixing portions 26 and 27 are a touch fastener with a surface A (hook surface).

When the electrically connecting unit 20 is attached to the back surface of the garment main body 30A (specifically, the surface of the fabric backing sheet 38 as described above (see FIG. 7), the cover portion 25 of the electrically connecting unit 20 is interposed between the skin of the subject who wears the biological signal monitoring garment 100A and the electrically connecting unit 20. By so doing, the cover portion 25 prevents the direct contact between the subject's skin and the electrically connecting unit 20. In other words, even though the unit cover 39 of the first example is not formed on the back surface of the front body 31A in the second example, the cover portion 25 eliminates the subject's discomfort due to the contact of the skin with the electrically connecting unit 20.

In the second example, when the electrically connecting unit 20 is detachably attached to the fabric backing sheet 38, the fixing portions 26 and 27 of the electrically connecting unit 20 are connected to the fabric backing sheet 38 after the instrument connectors 23a to 23d and the instrument connector holes 51 to 54 are aligned with each other.

As described above, in the second example, the cover portion 25 is formed on the back surface A1 of the electrically connecting unit 20, and the cover portion 25 is interposed between the electrically connecting unit 20, which is detachably attached to the fabric backing sheet 38 on the back surface of the garment main body 30A by the fixing portions 26 and 27, and the subject's skin, while the other components are the same as those in the first example. Therefore, not only the same action effects as those in the first example described above can be enjoyed, but also the operation required to sew the unit cover 39 to the back surface of the front body 31A in the garment main body 30A can be eliminated. As a result, the garment main body 30A can be made more easily than in the first example so that the cost required for manufacturing the biological signal monitoring garment 100A as well as the cost required for preparation can be reduced furthermore.

Third Example

Figure 11:
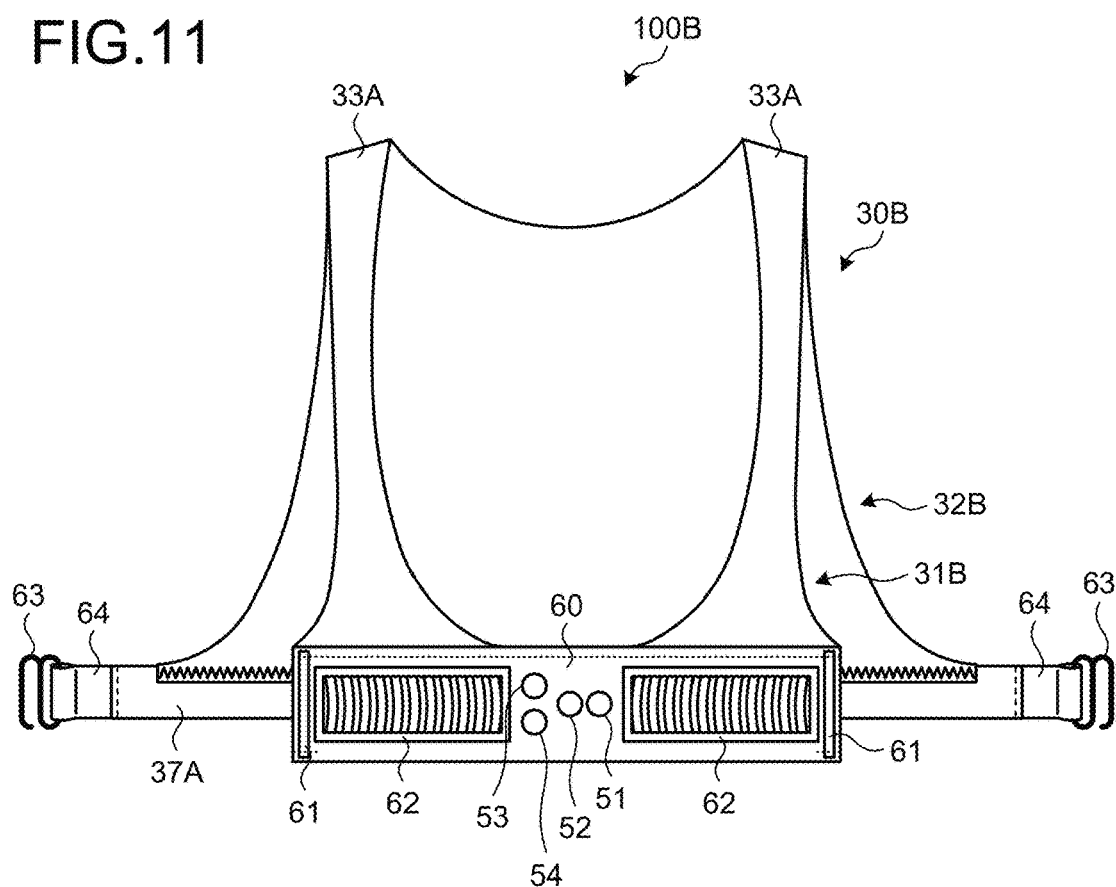
FIG. 11 is a drawing of one composition illustrating a biological signal monitoring garment according to a third example.
Figure 12:
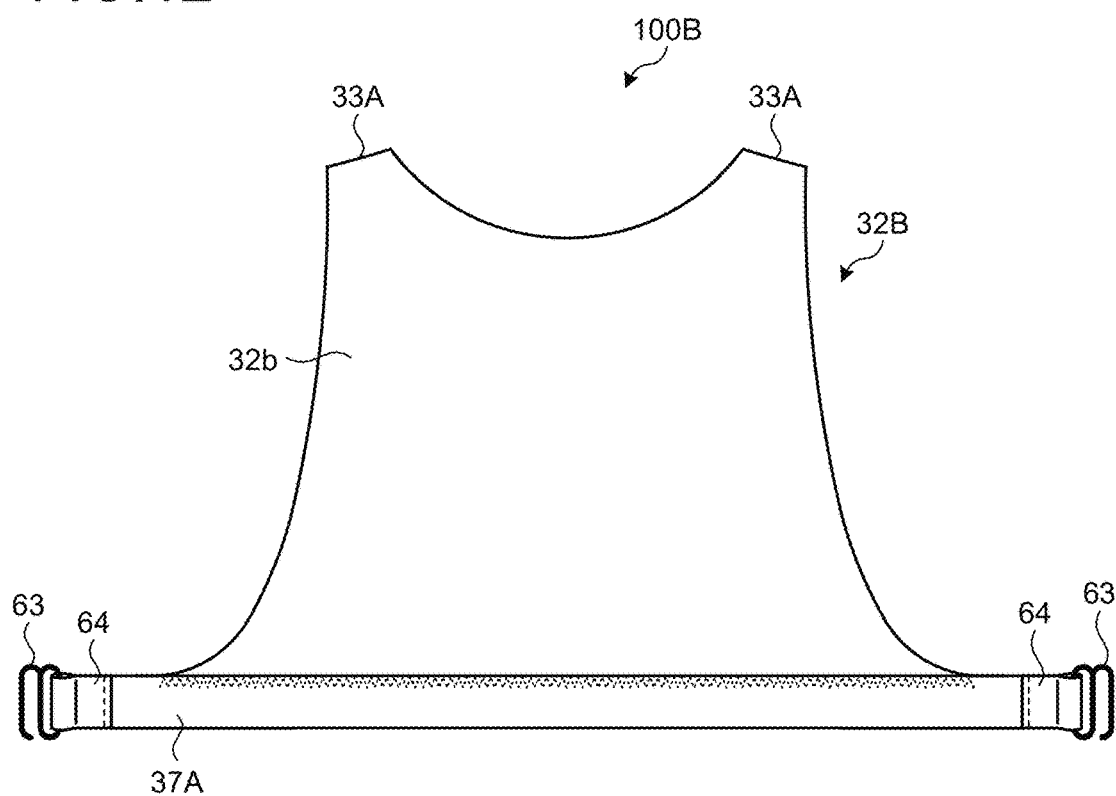
FIG. 12 is a drawing of one composition illustrating a backside of a garment main body applied to the biological signal monitoring garment according to the third example.

Next, a biological signal monitoring garment according to a third example will be described. FIG. 11 is a drawing of one composition illustrating the biological signal monitoring garment according to the third example. FIG. 11 is a drawing of a biological signal monitoring garment 100B according to the third example, viewed from the front surface side (front side) thereof. FIG. 12 is a drawing of one composition illustrating a back body of a garment main body applied to the biological signal monitoring garment according to the third example.

As illustrated in FIGS. 11 and 12, the biological signal monitoring garment 100B according to the third example includes a garment main body 30B instead of the garment main body 30 of the biological signal monitoring garment 100 according to the first example. The garment main body 30B according to the third example includes a front body 31B in place of the front body 31 in the garment main body 30 according to the first example, a back body 32B in place of the back body 32, and shoulder straps 33A in place of the shoulder straps 33. In the third example, the front body 31B of the garment main body 30B includes a unit storage body 60 in place of the torso portion 34 in the front body 31 in the first example. Although not illustrated in FIGS. 11 and 12, an electrically connecting unit in the third example is stored such that this can be taken out from and put in the unit storage body 60 in place of the electrically connecting unit 10 in the first example. As in the first example, the electrocardiograph 200 (see FIG. 1), which is one example of biological signal measurement instruments, is detachably attached to the front surface of the unit storage body 60. The back body 32B of the garment main body 30B includes a band-shaped (belt-shaped) elastic body 37A in place of the torso portion 35 and the elastic body 37 in the back body 32 of the first example. Other components are the same as those in the first example, and the same tags are attached to the same components. In the third example, a subject means a subject who wears the biological signal monitoring garment 100B according to the third example.

The front body 31B is integrally connected to the back body 32B by two shoulder straps 33A as illustrated in FIG. 11. At the opposite end (lower end) to the shoulder strap 33A in the front body 31B, the unit storage body 60 is formed as illustrated in FIG. 11. The unit storage body 60 has a bag-shaped structure long in the direction of the subject's torso girth and stores the electrically connecting unit in the third example such that this can be taken out and put in. The electrically connecting unit in the third example will be described later.

As illustrated in FIG. 11, the unit storage body 60 includes the same instrument connector holes 51 to 54 as those of the first example, as well as a pair of belt loops 61 and a pair of loop tapes 62. The instrument connector holes 51 to 54 are formed on a portion where the electrocardiograph 200 is attached in the surface of the unit storage body 60. The belt loops 61 are formed at each end of the unit storage body 60 in the longitudinal direction by sewing or the like. The loop tapes 62 are each formed by sewing or the like on the surface of the unit storage body 60 such that they are located between the instrument connector holes 51 to 54 and the belt loop 61. The belt loops 61 and the loop tapes 62 are formed preferably symmetrically with respect to the longitudinal center position of the unit storage body 60.

The back body 32B includes a dorsal portion 32b integrated with the front body 31B by two shoulder straps 33A as illustrated in FIGS. 11 and 12. The back body 32B does not have the torso portion 35 in the back body 32 in the first example, but includes the belt-shaped elastic body 37A. The elastic body 37A is a belt-shaped stretchable member long in the circumferential direction around the subject's torso girth, and is sewn directly to the lower end portion of the dorsal portion 32b of the back body 32B (the end portion opposite to the shoulder strap 33A) as illustrated in FIG. 12. At each of both ends of the elastic body 37A in the longitudinal direction, a hook 63 is formed as illustrated in FIGS. 11 and 12. The hook 63 is a member for detachably connecting the elastic body 37A in the state of being stretched in accordance with the length of the subject's torso girth to the unit storage body 60 of the front body 31B. For example, the hook 63 is connected to the elastic body 37A by a hook attachment tape 64. The elasticity characteristics and material of the elastic body 37A in the third example are the same as those of the elastic body 37 in the first example.

Figure 13A:
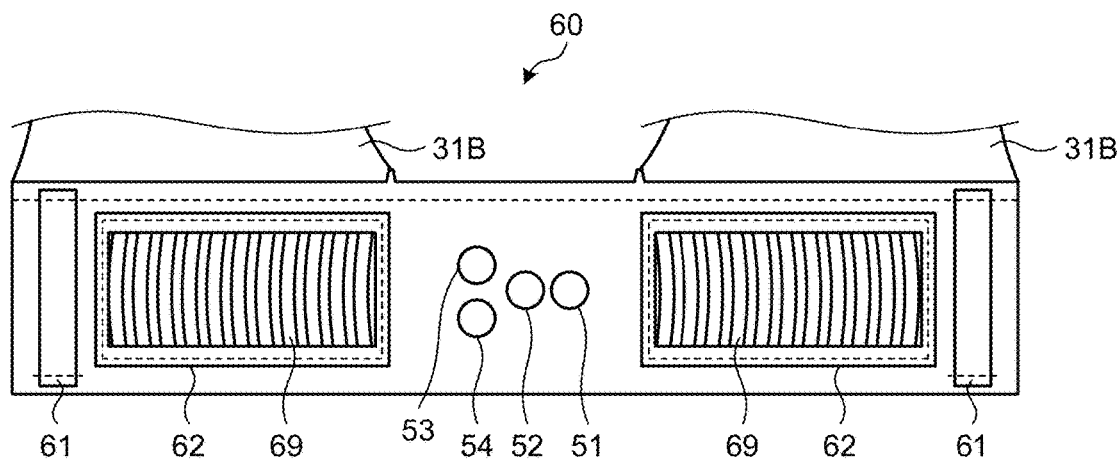
FIG. 13A is a drawing of one composition illustrating a unit storage body attached to a front body in the garment main body according to the third example.
Figure 13B:
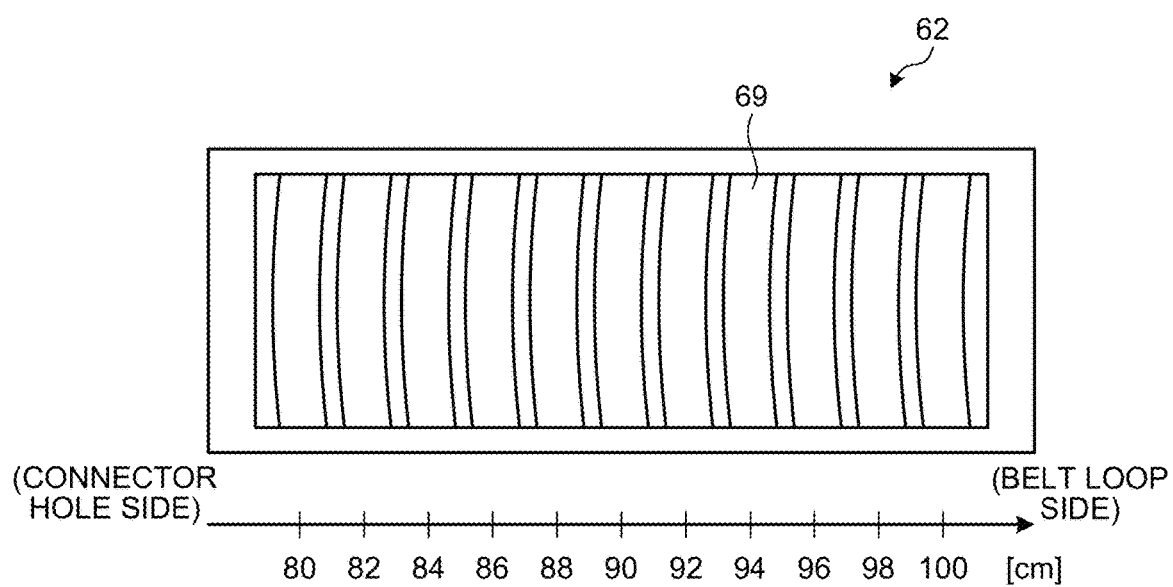
FIG. 13B is an enlarged view of one composition illustrating a loop tape in the unit storage body described in FIG. 13A.

FIG. 13A is a drawing of one composition illustrating the unit storage body attached to the front body of the garment main body according to the third example. FIG. 13A illustrates an enlarged view of the unit storage body 60 illustrated in FIG. 11 viewed from the front surface side (front side). FIG. 13B is an enlarged view of one composition illustrating the loop tape of the unit storage body illustrated in FIG. 13A. One loop tape 62 of a pair of loop tapes 62 is illustrated in FIG. 13B. As illustrated in FIG. 13A, a pair of the belt loops 61 and a pair of the loop tapes 62 are each sewn to the surface of the unit storage body 60, for example, in a symmetrical position across the instrument connector holes 51 to 54.

Each of the loop tapes 62 includes a plurality of loops 69 equally spaced from the side of the longitudinal center of the unit storage body 60 (the side of the instrument connector holes 51 to 54 in FIG. 13A) toward the side of the longitudinal end of the unit storage body 60 (the side of the belt loop 61 in FIG. 13A). For example, as illustrated in FIGS. 13A and 13B, 11 loops 69 are formed in each of the loop tapes 62 with an interval of 1 cm from the side of the instrument connector holes 51 to 54 toward the side of the belt loop 61. Although not specifically illustrated in the figures, the unit storage body 60 is formed with a fabric backing sheet having a non-elastic structure to prevent stretch- or contract-deformation of the unit storage body 60 due to the elasticity (elastic force) of the elastic body 37A. For example, this fabric backing sheet is attached to the inner surface of the fabric that makes up the bag-shaped unit storage body 60. The adhesive interlining or the like having a smooth surface is used as the fabric backing sheet to allow smooth loading and unloading of the electrically connecting unit to and from the unit storage body 60.

The connection of the elastic body 37A to the unit storage body 60 is realized by passing each side of the elastic body 37A through the belt loops 61 and then hanging the hooks 63 of the elastic body 37A to the loops 69 of the loop tapes 62. For example, when the subject's underbust size is 80 cm to 100 cm, the garment of the size M is used as the garment main body 30B suitable for this subject. For example, as illustrated in FIG. 13B, the loop tapes 62 each have 11 loops 69, each of which corresponds to the size of 80 cm to 100 cm.

Specifically, when the subject's underbust size is 88 cm, the left side hook 63 of the hooks 63 in both sides of the elastic body 37A is hung by insertion or the like to the "88 cm" loop 69 in the left side loop tape 62 of the loop tapes 62. The remaining right side hook 63 is hung by insertion or like to the "88 cm" loop 69 in the remaining left side loop tape 62. For example, as illustrated in FIG. 13B, the "88 cm" loop 69 is the fifth loop from the side of the instrument connector holes 51 to 54 (connector hole side) to the side of the belt loop 61 (belt loop side). When the subject's underbust size is 85 cm, the left side hook 63 of the hooks 63 in both sides of the elastic body 37A is hung by insertion or the like to the "86 cm" loop 69 in the left side loop tape 62 of the loop tapes 62. The remaining right side hook 63 is hung by insertion or like to the "84 cm" loop 69 in the remaining left side loop tape 62. For example, as illustrated in FIG. 13B, the "86 cm" loop 69 is the fourth loop from the connector hole side to the belt loop side. The "84 cm" loop 69 is the third loop from the connector hole side to the belt loop side. The order in which the hooks 63 on both sides of the elastic body 37A are hung may be from the right side, from the left side, or from both sides at the same time.

Figure 14:
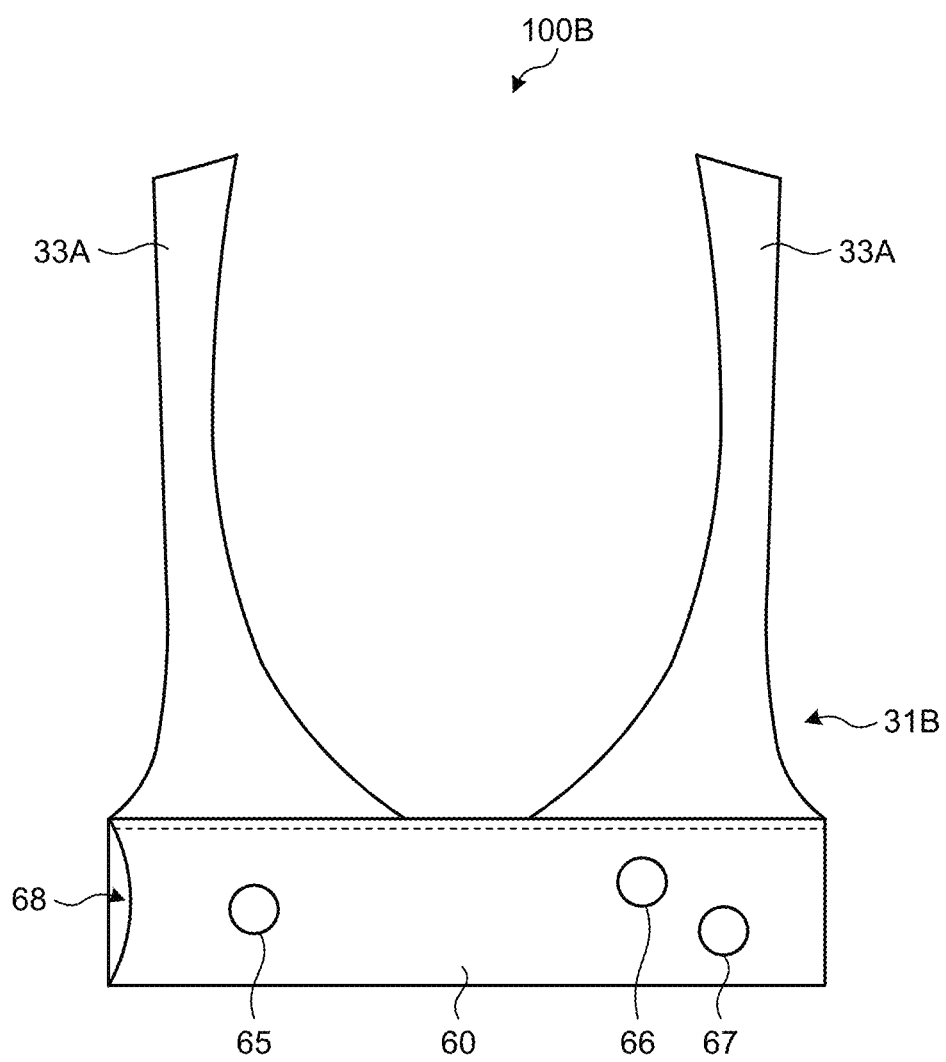
FIG. 14 is a drawing of one composition illustrating a back surface of the front body in the garment main body according to the third example.

Next, the back surface of the front body 31B in the garment main body 30B of the biological signal monitoring garment 100B according to the third example will be described. FIG. 14 is a drawing of one composition illustrating the back surface of the front body in the garment main body according to the third example. FIG. 14 illustrates the front body 31B of the biological signal monitoring garment 100B in the third example not attached with the electrically connecting unit, which is viewed from the back surface side.

As illustrated in FIG. 14, the bag-shaped unit storage body 60 is attached to the lower end of the front body 31B (the end opposite to the shoulder strap 33A) by sewing or the like. On the back surface of the unit storage body 60, there is a plurality (three in FIG. 14) of electrode holes 65 to 67. The unit storage body 60 includes a unit loading/unloading port 68 at one end of its longitudinal direction. The unit loading/unloading port 68 is an opening for loading and unloading the electrically connecting unit to/from the unit storage body 60. The unit storage body 60 detachably stores the electrically connecting unit by insertion thereof through the unit loading/unloading port 68. The stored electrically connecting unit can be easily taken out from the unit storage body 60 through the unit loading/unloading port 68.

Figure 15A:
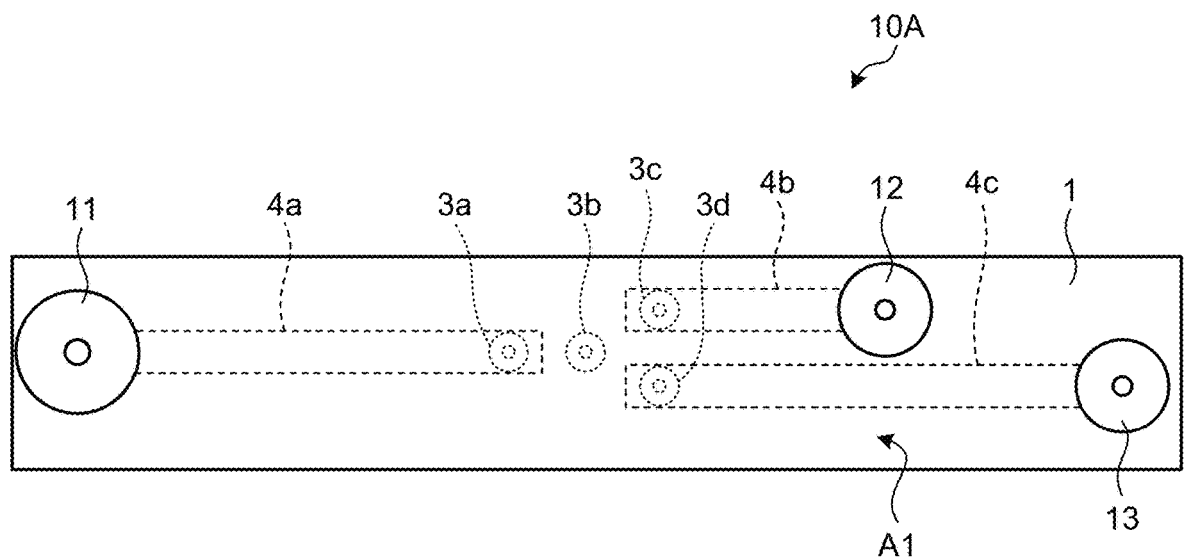
FIG. 15A is a drawing of one composition illustrating an electrode side of an electrically connecting unit applied to the biological signal monitoring garment according to the third example.
Figure 15B:
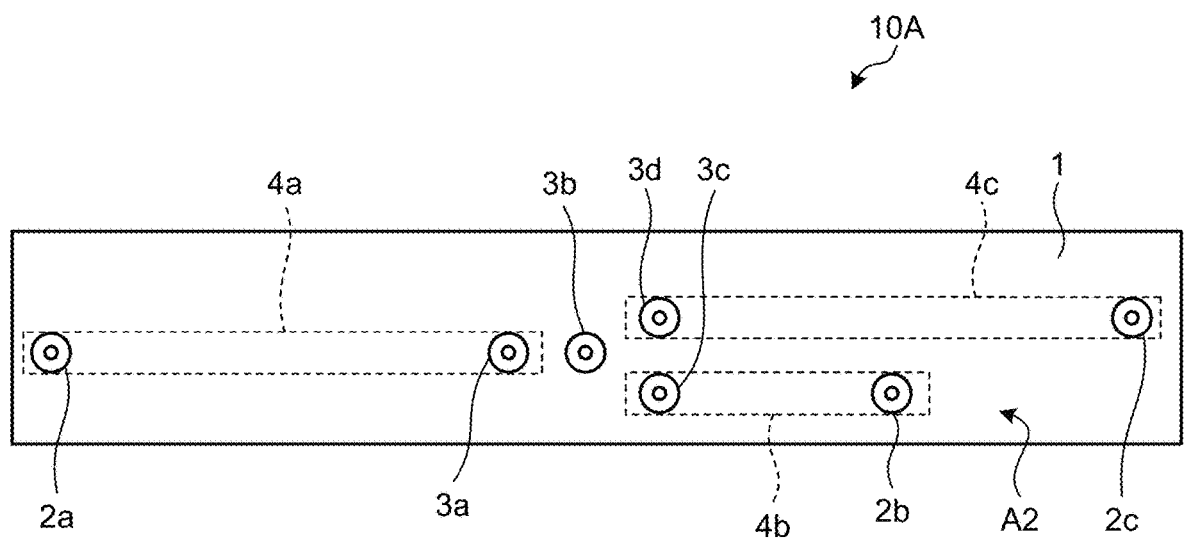
FIG. 15B is a drawing of one composition illustrating an instrument connector side of the electrically connecting unit applied to the biological signal monitoring garment according to the third example.

Next, the electrically connecting unit in the third example will be described. FIG. 15A is a drawing of one composition illustrating the electrode connector side of the electrically connecting unit applied to the biological signal monitoring garment according to the third example. FIG. 15B is a drawing of one composition illustrating the instrument connector side of the electrically connecting unit applied to the biological signal monitoring garment according to the third example.

As illustrated in FIGS. 15A and 15B, an electrically connecting unit 10A in the third example has the same composition as the electrically connecting unit 10 in the first example (see FIGS. 3A and 3B), except for the composition to be described below. In other words, the electrically connecting unit 10A in the third example includes the electrodes 11 to 13 that have been connected to the electrode connectors 2a to 2c, respectively, in advance. The electrically connecting unit 10A does not have the fixing portion 5 of the first example on the back surface A1 (electrode side) and the fixing portion 6 of the first example on the front surface A2 (instrument connector side). By omitting these fixing portions 5 and 6, the electrically connecting unit 10A can be smoothly put in and taken out from the unit storage body 60.

As illustrated in FIG. 14, the electrode holes 65 to 67 are formed on the back surface of the unit storage body 60. Therefore, the electrically connecting unit 10A can be put in and taken out from the unit storage body 60 without detaching the electrodes 11 to 13. The electrically connecting unit 10A is inserted into and stored inside the unit storage body 60 through the unit loading/unloading port 68 (see FIG. 14). At this time, the electrodes 11 to 13 of the electrically connecting unit 10A illustrated in FIG. 15A are exposed to the back surface of the garment main body 30B (specifically, the back surface side of the unit storage body 60) through the electrode holes 65 to 67 (see FIG. 14) from the inner surface side of the unit storage body 60. The instrument connectors 3a to 3d of the electrically connecting unit 10A illustrated in FIG. 15B are exposed to the front surface side of the garment main body 30B (specifically, the front surface side of the unit storage body 60) through the instrument connector holes 51 to 54 (see FIG. 11) from the inner surface side of the unit storage body 60. To the instrument connectors 3a to 3d in this exposed state, the electrocardiograph 200 (see FIG. 1) is connected as in the first example. As a result, the electrically connecting unit 10A is detachably attached inside the unit storage body 60, while the electrodes 11 to 13 to be in contact with the subject's skin are electrically connected to the electrocardiograph 200.

In the biological signal monitoring garment 100B according to the third example, the front body 31B, the back body 32B (especially the dorsal portion 32b), and the shoulder straps 33A constituting the garment main body 30B are formed of so-called free-cut fabrics that can be used in the as-cut state. These free-cut fabrics may also be used for the fabric of the unit storage body 60 possessed by the front body 31B. The free-cut fabric is a fabric having good elasticity. This is used also for underwear by rendering the functions of water absorption and quick drying. In general, the free-cut fabric is made of a material including a recycled fiber such as rayon and synthetic fibers such as nylon and polyurethane. In recent years, a natural fiber such as a cotton yarn has been developed as the material. In the third example, the free-cut fabric made of 68% nylon and 32% polyurethane and rendered with functions of water-absorption and quick drying is used. The greatest advantage of employing the free-cut fabric resides in that the sewing process using the binder tape, which is used in the first and second examples to prevent unraveling of the edges of the cut fabric, can be eliminated in the production of the biological signal monitoring garment. According to the biological signal monitoring garment 100B as mentioned above, in addition to the advantageous effects of the free-cut fabric, the same advantageous effects as those of the first and second examples can be enjoyed.

EXAMPLES

Next, specific examples of the biological signal monitoring garment will be described in detail. Our biological signal monitoring garment, however, is not limited to the Examples described below.

Comparative Example 1

In Comparative Example 1, based on the conventional technology described in JP '666, the biological signal monitoring garment was fabricated by connecting the electrode connector portions with the instrumentation connector portions by the lead wires such that these lead wires, electrode connector portions, and instrument connector portions could be insulated even if the body fabric would absorb a moisture due to a sweat, a rain or the like. In Comparative Example 1, the biological signal monitoring garment having the same shape as the first example (see FIGS. 1 and 2) was used.

In the fabrication of the biological signal monitoring garment of Comparative Example 1, components such as the lead wires, the electrode connector portions, and the instrument connector portions are directly attached to the garment main body. Because of this, the body fabric portion of the garment main body to which these components are attached, except for the electrodes that contact with the subject's skin, needs to be coated with a waterproof, electrically insulating material. Therefore, in Comparative Example 1, the manufacturing process to provide the garment main body with an insulation property is necessary. Hence, together with this, the manufacturing process becomes complex, thereby resulting in the increase in the manufacturing cost. Each working process and the time required for each process in fabrication of the biological signal monitoring garment of Comparative Example 1 are described in Table 1. The working processes required for fabrication of the biological signal monitoring garment of Comparative Example 1 include, for example, the wiring processing, the adhesive interlining processing, the snap button attachment, the seam taping processing, the wiring and connector attachment processing, the final garment attachment processing and the like. As can be seen in Table 1, among these processes, the time required for coating of the lead wires and the connector portions with the electrically insulating material (wiring and connector attaching process) accounts for more than half of the time required for the total working process in production of the biological signal monitoring garment according to Comparative Example 1.

TABLE 1

| Working process | Comparative Example 1 | Example 1 | Example 2 |
|---|---|---|---|
| Wiring processing | 0.4 min. | 1 min. | — |
| Adhesive interlining processing | 2.4 min. | — | — |
| Cover material processing | — | 3 min. | 0.5 min. |
| Snap button attachment | 5.4 min. | 2.5 min. | 3.2 min. |
| Seam taping processing | 6.9 min. | — | — |
| Cover material fabrication | — | 1.5 min. | 2 min. |
| Wiring and connector attachment processing | 22.3 min. | — | — |
| Final wear attachment processing | 1.8 min. | 1.5 min. | 1.5 min. |
| Total | 39.2 min. | 9.5 min. | 7.2 min. |

Example 1

In Example 1, the biological signal monitoring garment 100 in accordance with the first example was fabricated. In this process, the electrode connectors 2a to 2c, the instrument connectors 3a to 3d, and the lead wires 4a to 4c were integrated into the flexible sheet electrical insulator 1. By so doing, the electrically connecting unit 10 illustrated in FIGS. 3A and 3B was prepared. In fabrication of the electrically connecting unit 10, HITOE (registered trademark) Medical Lead Wire II was used for the lead wires 4a to 4c. Snap buttons manufactured by YKK Corp. were used for the electrode connectors 2a to 2c. Snap buttons manufactured by Hisanaga Seisakusho Co., Ltd. were used for the instrument connectors 3a to 3d. A polyolefin foam (TORAYPEF (registered trademark)) manufactured by Toray Industries, Inc. was used for the electrical insulator 1.

Each working process and the time required for each process in fabrication of the biological signal monitoring garment of Example 1 are described in Table 1. Referring to Table 1, comparison of Example 1 with Comparative Example 1 was made for the working process and the time required for each working process. As a result, in Example 1, the wiring and connector attaching process (coating of the body fabric portion in the garment main body, the lead wires, and the connector portions by the electrically insulating material) that was necessary in Comparative Example 1 is not necessary so that the time required for the working process could be reduced compared to Comparative Example 1. Specifically, the working process for fabricating the biological signal monitoring garment of Example 1 can be aggregated in the working process required for fabricating the electrically connecting unit 10 by integrating the electrode connectors 2a to 2c, the instrument connectors 3a to 3d, and the lead wires 4a to 4c into the electrical insulator 1. As a result, the time required for the entire working process in Example 1 can be reduced to ¼ or less of that in Comparative Example 1. This makes it possible to significantly reduce the cost of the biological signal monitoring garment in Example 1 as compared to Comparative Example 1.

Example 2

In Example 2, the biological signal monitoring garment 100A in accordance with the second example was fabricated.

In this process, the electrode connectors 22a to 22c, the instrument connectors 23a to 23d, and the lead wires 24a to 24c were integrated into the sheet electrical insulator 21, typically represented by a flexible printed wiring board or the like; by so doing, the electrically connecting unit 20 illustrated in FIGS. 8A and 8B was prepared. Upon fabricating the electrically connecting unit 20, for the electrical insulator 21, a flexible board made of a polyester film having a thickness of 50 µm was used as the base film board. Then, the electrically conductive portions such as the lead wires 24a to 24c were formed on the electrical insulator 21 by printing a silver nano-ink onto this flexible board followed by copper plating. The resulting electrically conductive portions were then covered with a solder resist. With this, the insulation property of the electrically conductive portions of the electrical insulator 21 can be kept. The electrode connectors 22a to 22c and the instrument connectors 23a to 23d were the same as the components in Example 1. To avoid the direct contact between the electrical insulator 21 and the subject's skin, the electrode connector side of the electrical insulator 21 (back surface A1) was covered by the cover portion 25 formed of a blend fabric of polyester with cotton. On the instrument connector side (front surface A2) of the electrically connecting unit 20, a touch fastener with a surface A (hook surface) is bonded to the garment main body such that this can be detachably attached to the garment main body. On the attaching surface of the electrically connecting unit 20 in the garment main body, a touch fastener with a surface B (loop surface), which is relatively less irritating to the subject's skin, is sewn.

Each working process and the time required for each process in fabrication of the biological signal monitoring garment of Example 2 are described in Table 1. Referring to Table 1, a comparison among Example 1, Example 2, and Comparative Example 1 was made with regard to the working process and the time required for each working process. As a result, in Example 2, as in Example 1, because the wiring and attaching process of the connectors required for Comparative Example 1 is not necessary, the time required for the entire working process can be reduced compared to Comparative Example 1. In addition, in Example 2, the flexible board having the electrically conductive portions printed is used as the board for the electrically connecting unit 20 so that the wiring process of the lead wires 4a to 4c that were required in fabrication of the electrically connecting unit 10 in Example 1 is not necessary. On top of this, in Example 2, the cover portion 25 is formed on the electrically connecting unit 20 as illustrated in FIG. 8A so that the time required for the working process of cover material processing is reduced compared to Example 1 in which the unit cover 39 (see FIG. 4) is formed on the garment main body 30. As a result, as can be seen in Table 1, the time required for the entire working process in Example 2 can be made shorter compared to not only Comparative Example 1 but also Example 1.

Example 3

In Example 3, the biological signal monitoring garment was worn by a subject, and the biological signal of this subject was measured. The biological signal monitoring garment 100A according to the second example was used as the biological signal monitoring garment in Example 3, in which the Holter electrocardiograph (EV-301, manufactured by Parama-Tech Co., Ltd.) was used as the biological signal measurement instrument applied to this garment. The electrocardiographic signal was measured in a male subject in a normal life environment for 7 days, followed by additional measurement of the electrocardiographic signal for about 3 days continuously. In Example 3, HITOE (registered trademark) Medical Lead Wire II manufactured by Toray Medical Co., Ltd. was used as the electrocardiograph wire connected to the biological signal measurement instrument, and HITOE (registered trademark) Medical Electrode II manufactured by Toray Medical, Co., Ltd. was used as the electrocardiograph electrodes (electrodes 11 to 13 illustrated in FIG. 7) to be in contact with the subject's skin. In the biological signal monitoring garment of Example 3, the elastic body 37 applied to the garment main body 30A was a flat rubber having the width of 4 cm and the length of 40 cm (LY-40, manufactured by Kitani Co., Ltd.). A two-way tricot (polyester/polyurethane) was used as the material of the garment main body 30A. The length of the torso girth of the subject's solar plexus portion is between 80 cm and 100 cm (size M). The stretching rate of the elastic body 37 in the longitudinal direction is 30%, and the force obtained by the elastic body 37 in the stretched state at this stretching rate is 5.9 N.

In Example 3, the electrocardiographic analysis was conducted on the basis of the electrocardiographic signal measured from the subject who wears the biological signal monitoring garment 100A. The software used in analysis of the electrocardiogram was the long time Holter electrocardiogram analysis viewer (NEY-HEA 3000), manufactured by Nexis Co., Ltd. FIG. 16 is a drawing illustrating one example of the electrocardiogram analysis reports obtained in Example 3. The electrocardiogram analysis report illustrated in FIG. 16 is the cover section of the report on the electrocardiogram analysis performed on the basis of the result of the electrocardiogram signal measurement for an additional three days in the subject. In this electrocardiogram analysis report, the electrocardiogram analysis result is summarized. Specifically, as described in FIG. 16, in this electrocardiogram analysis report, the analysis results regarding the heartbeat information, the PVC (premature ventricular contraction), the PAC (premature atrial contraction), the ST level, the atrial fibrillation, and the trial flutter are summarized in one sheet. The electrocardiogram acquisition rate based on the electrocardiogram signal obtained during the additional measurement time (about 71 hours) is 99.8%, indicating that from the subject the biological signal monitoring garment 100A produced the stable electrocardiogram signal with which the electrocardiogram could be analyzed over a long period of time.

Figure 17:
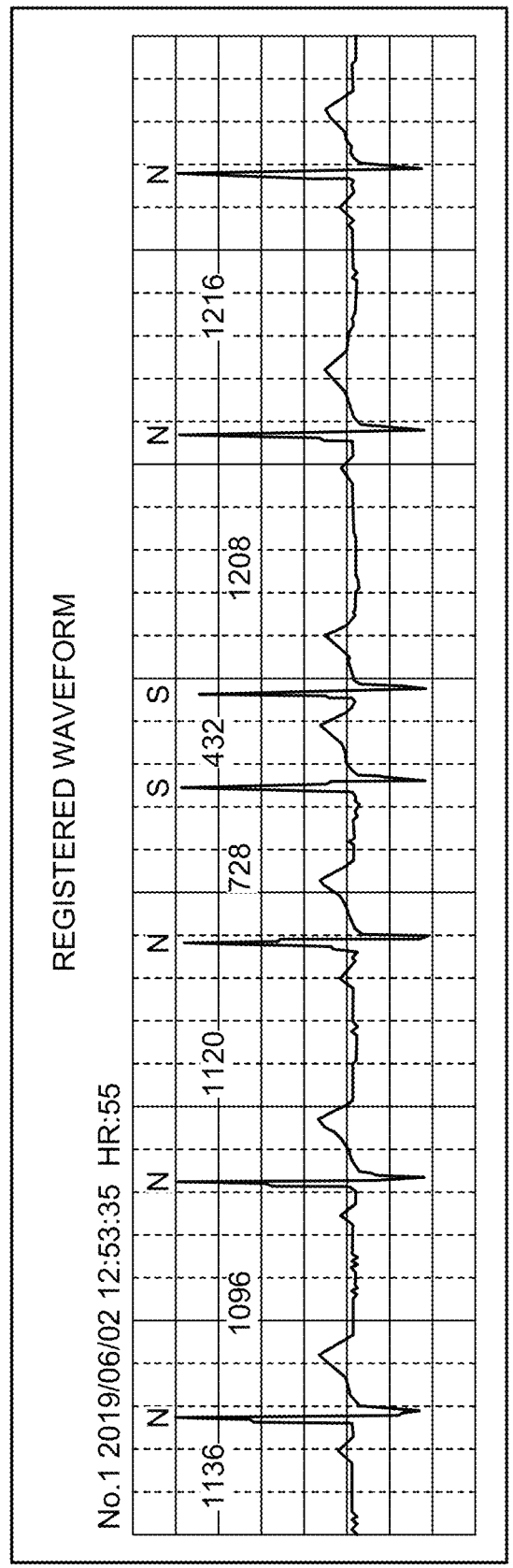
FIG. 17 is a drawing illustrating one example of registered waveforms in the electrocardiogram analysis report obtained in Example 3.
Figure 18:
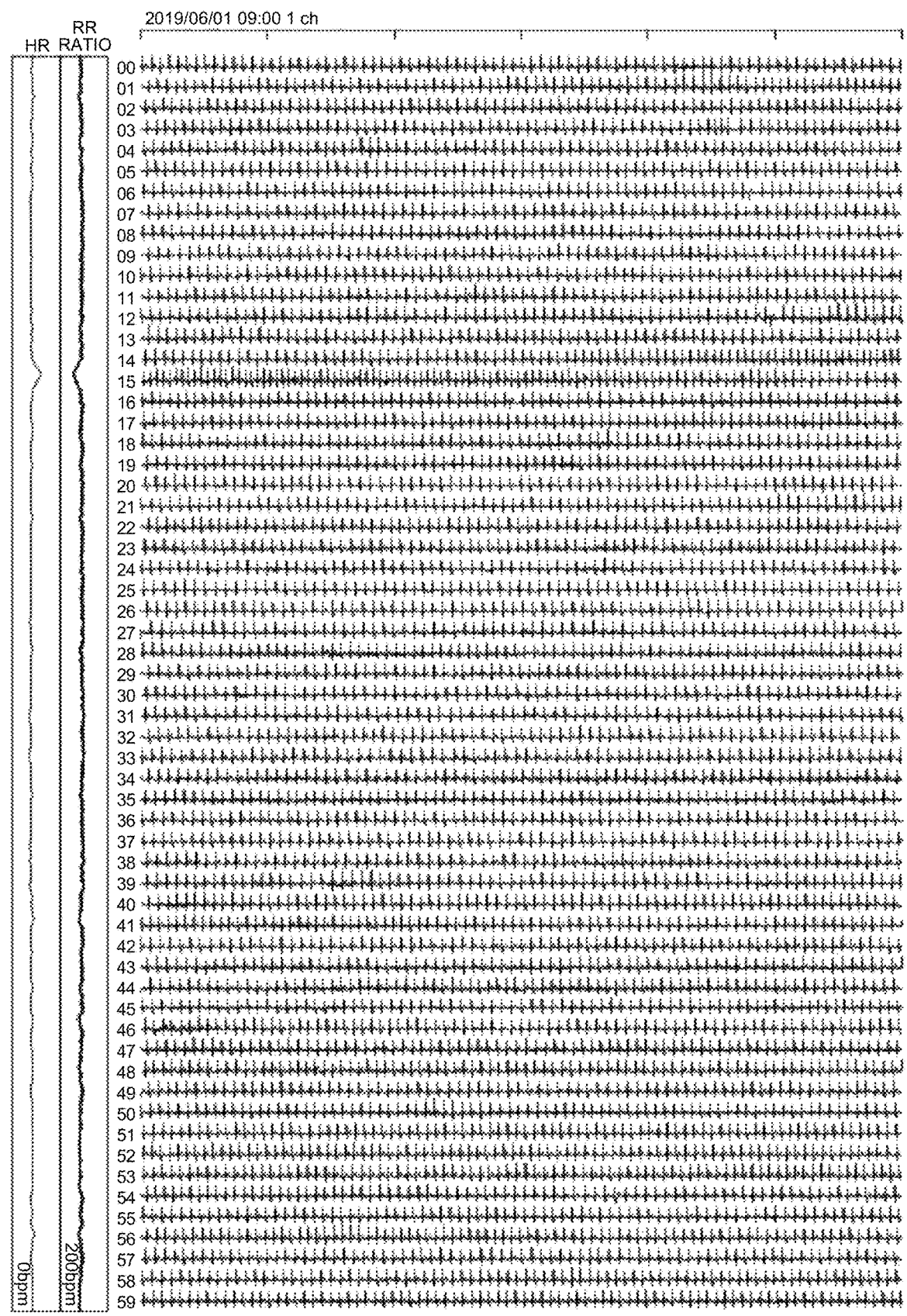
FIG. 18 is a drawing illustrating one example of compressed waveforms in the electrocardiogram analysis report obtained in Example 3.

FIG. 17 is a drawing illustrating one example of registered waveforms in the electrocardiogram analysis report obtained in Example 3. FIG. 17 illustrates a part of the registered waveform (the subject's electrocardiogram waveform) in this electrocardiogram analysis report. As can be seen FIG. 17, a typical sinus rhythm is obtained in the registered waveform, in which the P wave, the QRS wave, and the T wave can be clearly read. FIG. 18 is a drawing illustrating one example of compressed waveforms in the electrocardiogram analysis report obtained in Example 3. The compressed waveform seen in FIG. 18 is a one-hour electrocardiogram of the subject summarized in a single graph.

In Example 3, the subject's electrocardiogram signal was measured using the biological signal monitoring garment 100A according to the second example, and then the electrocardiogram analysis was performed. The results of the electrocardiogram signal measurement and of the electrocardiogram analysis can be obtained as well even when using the biological signal monitoring garments 100 and 100B according to the first and third examples, respectively.

Our garments are not limited by the first to third examples described above. Hence, this disclosure also includes compositions in which each of the component elements described above is combined as appropriate. All other examples, operational techniques and the like made by those skilled in the art or the like, based on the first to the third examples described above are included in the scope of this disclosure.

INDUSTRIAL APPLICABILITY

As described above, our biological signal monitoring garment is useful for monitoring the subject's biological signal, and is particularly suitable as the inexpensive biological signal monitoring garment that can comfortably, easily, and stably measure the biological signal with less noise over a period desired by the subject who is being engaged in a daily life.

The invention claimed is:

1. A biological signal monitoring garment comprising:
    a plurality of electrodes configured to contact skin of a subject;
    a garment main body configured to be worn by the subject, the garment main body including:
    a front body torso portion;
    a back body torso portion provided with a band-shaped elastic body; and
    a fabric backing sheet having a non-elastic structure, the fabric backing sheet being provided in the front body torso portion, and
    a sheet electrical insulator having flexibility, the electrical insulator being configured to be detachably attached to the front body torso portion to interpose the fabric backing sheet between the electrical insulator and the front body torso portion, wherein
    the electrical insulator has a back surface and a front surface, the back surface facing the skin of the subject and the front surface being away from the skin when the garment main body is worn by the subject,
    a plurality of electrode connectors to which the plurality of electrodes are connected to input a biological signal of the subject are arranged in the back surface of the electrical insulator,
    an instrument connector configured to output the biological signal that is input to the plurality of electrode connectors is arranged in the front surface of the electrical insulator, and
    an electrical conductor configured to electrically connect the plurality of electrode connectors to the instrument connector is arranged in the electrical insulator.

2. The biological signal monitoring garment according to claim 1, further comprising a fabric member covering the back surface of the electrical insulator other than the electrode connectors.

3. The biological signal monitoring garment according to claim 1, wherein the electrodes comprise an electrically conductive fiber structural body.

4. The biological signal monitoring garment according to claim 3, wherein the electrodes each are composed of a nanofiber having a fiber diameter of 10 nm or more to 5000 nm or less.

5. The biological signal monitoring garment according to claim 1, wherein the electrodes each comprise an electrically conductive sheet having an adhesion strength of 200 g/20 mm or less, the adhesion strength being measured with a 90-degree peel-off method in accordance with JIS-Z0237.

6. The biological signal monitoring garment according to claim 1, wherein
    the front body torso portion includes first side tabs at both ends of the front body torso portion, the first side tabs including a first joint portion,
    the back body torso portion includes second side tabs at both ends of the back body torso portion, the second side tabs including a second joint portion to which the first joint portion is detachably connected, and
    the front body torso portion and the back body torso portion are annularly connected to each other when the first joint portion is connected to the second joint portion.

7. The biological signal monitoring garment according to claim 6, wherein
    the back body torso portion is stretchable and a hollow band,
    the elastic body is incorporated into the back body torso portion in a longitudinal direction of the back body torso portion, and
    the elastic body is arranged between the second side tabs.

8. The biological signal monitoring garment according to claim 7, wherein the fabric backing sheet includes an instrument connector hole corresponding to the instrument connector.

9. The biological signal monitoring garment according to claim 1, wherein
    the back body torso portion is integrated with the elastic body,
    the elastic body includes hooks at both ends of the elastic body,
    the front body torso portion has a bag-shaped structure having an opening, the bag-shaped structure storing the electrical insulator through the opening,
    the front body torso portion includes a loop tape including a plurality of loops to which the hooks are detachably attached, and
    the plurality of loops are equally spaced in a longitudinal direction of the front body torso portion.

10. The biological signal monitoring garment according to claim 9, wherein
    the front body torso portion includes a belt loop, and
    the elastic body is connected to the front body torso portion when the elastic body passes through the belt loop and the hooks are hanged to the plurality of loops.

11. The biological signal monitoring garment according to claim 9, wherein the fabric backing sheet is attached to an inner surface of the front body torso portion.

12. The biological signal monitoring garment according to claim 9, wherein the front body torso portion include:
    a plurality of electrode holes corresponding to the plurality of electrodes; and
    an instrument connector hole corresponding to the instrument connector.

13. The biological signal monitoring garment according to claim 12, wherein
    the belt loop is a pair of belt loops at both ends of the front body torso portion,
    the loop tape is a pair of loop tapes that are arranged between the pair of belt loops, and
    the instrument connector hole is arranged between the pair of loop tapes.

* * * * *